United States Patent
Beaudry et al.

(10) Patent No.: US 10,894,066 B2
(45) Date of Patent: *Jan. 19, 2021

(54) AMNION DERIVED THERAPEUTIC COMPOSITIONS AND METHODS OF USE

(71) Applicant: Amnio Technology LLC, Phoenix, AZ (US)

(72) Inventors: Christian Beaudry, Phoenix, AZ (US); Bruce Werber, Phoenix, AZ (US); Terrell Suddarth, Winchester, TN (US)

(73) Assignee: Amnio Technology LLC, Phoenix, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/257,870

(22) Filed: Sep. 6, 2016

(65) Prior Publication Data

US 2016/0375064 A1    Dec. 29, 2016

Related U.S. Application Data

(63) Continuation-in-part of application No. PCT/US2015/019318, filed on Mar. 6, 2015, and a continuation-in-part of application No. PCT/US2015/019294, filed on Mar. 6, 2015, and a continuation-in-part of application No. PCT/US2015/019311, filed on Mar. 6, 2015, and a continuation-in-part of application No. 14/853,889, filed on Sep. 14, 2015, now Pat. No. 9,814,746, which is a continuation-in-part of application No. 14/593,415, filed on Jan. 9, 2015, now Pat. No. 9,132,156.

(60) Provisional application No. 61/949,066, filed on Mar. 6, 2014, provisional application No. 61/949,135, filed on Mar. 6, 2014, provisional application No. 61/949,087, filed on Mar. 6, 2014, provisional application No. 61/949,106, filed on Mar. 6, 2014, provisional application No. 62/012,394, filed on Jun. 15, 2014.

(51) Int. Cl.
A61K 35/50    (2015.01)

(52) U.S. Cl.
CPC .................. A61K 35/50 (2013.01)

(58) Field of Classification Search
CPC .................................... A61K 35/50
See application file for complete search history.

(56) References Cited

U.S. PATENT DOCUMENTS

| | | | |
|---|---|---|---|
| 8,932,805 B1* | 1/2015 | Brahm | C12N 5/0605 435/1.3 |
| 9,827,293 B2* | 11/2017 | Koob | A61K 38/1866 |
| 2004/0048796 A1 | 3/2004 | Hariri et al. | |
| 2004/0057938 A1 | 3/2004 | Ghinelli | |
| 2005/0042595 A1* | 2/2005 | Haas | C12N 5/0605 435/2 |
| 2007/0020225 A1 | 1/2007 | Abramson et al. | |
| 2008/0286378 A1 | 11/2008 | Behren | |
| 2009/0004160 A1 | 1/2009 | Park et al. | |
| 2009/0098214 A1 | 4/2009 | Nanbu et al. | |
| 2010/0272782 A1 | 10/2010 | Owens et al. | |
| 2012/0189586 A1 | 7/2012 | Harrell | |
| 2012/0315259 A1 | 12/2012 | Friedlander | |
| 2013/0095061 A1 | 4/2013 | Cohen et al. | |
| 2013/0267008 A1 | 10/2013 | Shon et al. | |
| 2013/0280344 A1 | 10/2013 | Tseng et al. | |
| 2013/0280801 A1 | 10/2013 | Sun | |
| 2014/0050788 A1 | 2/2014 | Daniel et al. | |
| 2014/0255357 A1 | 9/2014 | Burt | |
| 2014/0255496 A1 | 9/2014 | Daniel et al. | |
| 2014/0271776 A1 | 9/2014 | Vines et al. | |
| 2014/0295554 A1 | 10/2014 | Kim et al. | |
| 2015/0216912 A1* | 8/2015 | Koob | A61K 35/50 424/93.7 |

FOREIGN PATENT DOCUMENTS

WO    WO 12/091206    *    7/2012    ............. C12N 5/074

* cited by examiner

*Primary Examiner* — Allison M Fox
(74) *Attorney, Agent, or Firm* — Invention To Patent Services; Alex Hobson

(57) ABSTRACT

Therapeutic compositions are described for the treatment of a variety of conditions including heart, eye, lungs, organs, joints, dermal, nerve, and the like. A therapeutic composition may be a fluid comprising amniotic fluid or micronized amniotic particles. A therapeutic composite may be a dispersion of micronized amniotic membrane combined with a fluid, such as plasma, saline, amniotic fluid, combinations thereof and the like. In another embodiment, the therapeutic composite is a mixture of micronized amniotic membrane particles combined with an amniotic rich stem cell fluid. An amniotic rich or concentrated stem cell fluid comprises at least $0.5 \times 10^6$ amniotic stem cells per milliliter of fluid or composition. A therapeutic composite may be used to treat any number of conditions through topical application, surgical introduction, and/or injection.

2 Claims, 25 Drawing Sheets

Baseline

Follow Up at 6 days

Follow Up at 13 days

Pre injection: painful scar & bedridden

18 hours post injection
- no pain, normal turgor
- walking without pain 6 months post-op

AMNION DERIVED THERAPEUTIC COMPOSITIONS AND METHODS OF USE

CROSS REFERENCE TO RELATED APPLICATIONS

This application is a continuation in part of PCT/US2015/019318, having an international filing date of Mar. 6, 2015, which claims the benefit of U.S. provisional patent applications Nos. 61/949,066, and 61/949,135, both filed on Mar. 6, 2014; this application is also a continuation in part of PCT patent application no. US2015/019294, having an international filing date of Mar. 6, 2015, which claims the benefit of U.S. provisional patent applications no. 61/949,087, and 61/949,106, both filed on Mar. 6, 2014; this application is also a continuation in part of PCT patent application no. US2015/019311, having an international filing date of Mar. 6, 2015, which claims the benefit of U.S. provisional patent applications no. 61/949,087, 61/949,106, 61/949,066, and 61/949,135 all filed on Mar. 6, 2014; this application is also a continuation in part of U.S. patent application Ser. No. 14/853,889, filed on Sep. 14, 2015 and currently pending, which is a continuation in part of U.S. patent application Ser. No. 14/593,415 filed on Jan. 9, 2015 and issued as U.S. patent application Ser. No. 9,132,156, which claims the benefit of U.S. provisional patent application No. 62/012,394 filed on Jun. 15, 2014; the entirety of all applications and patents listed above are hereby incorporated by reference herein.

BACKGROUND OF THE INVENTION

Field of the Invention

The present invention relates to therapeutic compositions derived from amnion materials and methods of use.

SUMMARY OF THE INVENTION

Amniotic membranes are being used in clinical trials to treat a wide range of conditions. Amniotic membranes are typically placed directly on a treatment location, such as a wound or incision. In many cases however, amniotic membranes lack the proper architecture and cell viability to effectively provide the desired therapeutic responses, such as tissue regenerations, immunomodulation, anti-inflammatory and antifibrotic. Most amniotic membranes are dehydrated and cryogenically preserved. In other cases, the amniotic membranes are sterilized in a manner that damages the tissue and/or reduces cell viability. For example, many amniotic membranes are processed with a glutaraldehyde which is known to significantly reduce cell viability. In many treatment applications, it is desirable to provide a high concentration and/or specific type or blend of stem cells. In addition, some therapeutic composites comprise components from two or more donors thereby limiting their use.

The invention is directed to therapeutic compositions that, in one embodiment, comprise a therapeutic fluid comprising amniotic fluid. An amniotic fluid may comprise any number of cells, including stem cells, growth factors, proteins and the like. In one embodiment, a therapeutic fluid comprises an amniotic fluid that is acellular. In another embodiment, a therapeutic composition comprises a matrix component, such as an amniotic membrane. In still another embodiment, a therapeutic composition comprises a matrix component and a fluid component, wherein a fluid component may be imbibed into or coated onto one or more surfaces of the matrix component. In an exemplary embodiment, a therapeutic composition comprises an amniotic membrane in the matrix component and comprises amniotic fluid in the fluid component.

In an exemplary embodiment, the therapeutic composition, as described herein, comprises a plurality of amniotic stem cells, and may comprise a high concentration, such as greater than $0.5 \times 10$ per milliliter of the therapeutic fluid component within the therapeutic composition. A therapeutic fluid component may also be acellular, such as an acellular amniotic fluid. An acellular amniotic fluid is described in U.S. application Ser. Nos. 14/593,415, and 14/853,889 to Amnio Technology LLC; the entirety both of which are incorporated by reference herein. A therapeutic fluid component may be referred to herein as simply a fluid component for brevity. In another embodiment, a fluid component comprises amniotic membrane that has been micronized and dispersed in a fluid. In one embodiment, a fluid component is a dispersion of micronized amniotic membrane combined with a fluid, such as plasma, saline, amniotic fluid, combinations thereof and the like. In another embodiment, a fluid component comprises a mixture of micronized amniotic membrane particles combined with an amniotic stem cell concentrated fluid. In still another embodiment, a therapeutic fluid consists essentially of a concentrated amniotic fluid wherein the quantity of amniotic stem cells is increased. The amniotic stems cells in the therapeutic composite, as described herein, may be derived from amniotic fluid and the stem cells may be concentrated by a centrifuge process. Additional fluids and agents may be added to the amniotic stem cells such as plasma, Plasma Lyte-A, from Baxter Inc., saline and the like. The concentration of amniotic stems cells in one milliliter of a fluid component of an exemplary therapeutic composition, as described herein, may be about $0.5 \times 10^6$ or more, $1.0 \times 10^6$ or more, $5.0 \times 10^6$ or more, $10 \times 10^6$ or more and any range between and including the concentrations values provided. A high concentration of amniotic stems cells may greatly improve the effectiveness of the therapeutic composition for many applications. The therapeutic composition, as described herein, may comprise endothelial cells, mesenchymal stem cells, amniotic fluid stem cells, fibroblasts, proteins, keritinocytes, epithelial and/or epidermal cells, paratenacytes, keratinocytes, epithelial and/or epidermal cells, paratenacytes, keratinocytes and growth factors. In some embodiments, protein markers for mesenchymal stem cells may be analyzed to quantify the various types of cells within the therapeutic composition. Flow cytometry may be used to identify proteins, CD44, CD105, CD73 and CD90. In one embodiment, a therapeutic, composition comprises at least 30% of mesenchymal stem cells as identified by CD73. Mesenchymal stem cells indicated by CD73 proteins may be more mobile and provide a more therapeutic effect that mesenchymal stem cells identified by the other markers. A therapeutic fluid component, as described herein, may comprise anti-inflammatory nano-particles and/or statins, HMO-CoA reductase inhibitors to reduce inflation at a treatment location.

In some embodiments, a therapeutic composition is doped with progenitor cells and the progenitor cells may be multipotent progenitor cells and/or pluripotent progenitor cells. Progenitor cells may be derived from a patient to be treated, such as from a stromal vascular fraction. Vascular fraction cells and/or progenitor cells may be included with a therapeutic composite to further improve effectiveness. Progenitor cells may be autologous or allogeneic.

In some embodiments, a therapeutic composition, or a fluid component thereof, a cellular controlled amniotic fluid therapeutic composition is prepared by removing the cells from an amniotic fluid and then adding back in a known amount of these removed cells to a desired concentration. For example, an amniotic fluid may be first filtered to remove large debris and subsequently centrifuged to separate the cells from the amniotic fluid component. The fluid component may further be processed, such as by filtration to remove any particles. In addition, the amniotic fluid component may be concentrated or diluted as desired. The amniotic fluid component may be concentrated by allowing some of the liquid to evaporate, thereby increase the concentration of growth factors and proteins within the amniotic fluid component. Conversely, the amniotic fluid component may be diluted by the addition of liquid, such as water or saline solution, for example. An exemplary therapeutic composition may be prepared by adding removed cells to the amniotic fluid component in a desired concentration, as described herein. A concentration of removed amniotic fluid cells may be added in a concentration of about $0.5 \times 10^6$ or more, $1.0 \times 10^6$ or more, $2.0 \times 10^6$ or more $5.0 \times 10^6$ or more, $10.0 \times 10^6$ or more $20 \times 10^6$ or more per ml of cellular controlled amniotic fluid, and any range between and including the concentration percentages provided. A high concentration of amniotic stems cells may greatly improve the effectiveness of the therapeutic composition for many applications. The higher concentrations may be achieved by concentration of the amniotic fluid. When the amniotic fluid is concentrated, such as by removal of liquid by the application of heat, the removed cells will be protected from this adverse processing, thereby maintaining viability. In addition, other cells may be added to the amniotic fluid component including, but not limited to, stem cells from a stromal vascular fraction, bone marrow, progenitor cells and the like. These donor cells may be acquired from a donor that will later receive treatment utilizing the therapeutic composition incorporating the donor cells. A cryo-protectant solution such as CryoStor 10, available from Sigma-Aldrich, may be added to the amniotic fluid component to preserve the viability of the cells during cryopreservation. A cryo-protectant may be added prior to centrifuging, or to the fluid component after separating out the cells, to the separated cells, or after a desired concentration of cells is added back to the fluid component. The cellular controlled amniotic fluid therapeutic composition may be cryopreserved down to below about 4° C. to preserve cell viability. In an exemplary embodiment, a high percentage of cells within the cellular controlled amniotic fluid therapeutic composition may be viable after thawing from a cryopreserved state, such as about 50% of more, about 75% or more, about 85% or more, about 90% or more and most preferably about 95% or more, and any range between and including the percentages provided.

A fluid component, as described herein, may comprise particles and/or a concentration of amniotic stem cells. The particles within the fluid component may comprise micronized amniotic membrane. The micronized amniotic membrane may comprise hydrated mammalian amniotic tissue having a percent hydration of at least about 25%, at least about 50%, at least about 75% by weight or any range between the concentrations provided. Amniotic membrane maintained in a hydrated state may provide for more viable and regenerative properties. Amniotic membranes that are lyophilized have a great reduction in cell viability. The particles in the fluid component, as described herein, may consists essentially of amniotic membrane and be substantially free of chorion. The amnion layer may be removed from the chorion prior to processing. In one embodiment, the amniotic membrane particles consist essentially of epithelium wherein the concentration of the epithelium is about 70% or more, for example. The particles consisting essentially of epithelium may comprise stem cells and tissue that may substantially surround the stem cells.

An amniotic membrane, or portion thereof, may be micronized while in a hydrated state thereby improving the viability of cells. The amniotic membrane particles may be derived from dehydrated and/or decellularized amniotic tissue however. In addition, the amniotic membrane may be cryo-fractured, such as with a blunt object to minimize shear and damage to tissue, thereby improving therapeutic effectiveness. Particles of amniotic membrane may have any suitable particle size, average particle size and particle sized distribution. For example, the amniotic membrane derived particles, or micronized particles, may have a particle size, or an average particle size of no more than about 10 µm, no more than about 5 µm, no more than about 2 µm, no more than about 1 µm, no more than about 0.5 µm and any range between and including the average particle sizes provided. The particle size of the amniotic membrane particles can be determined through any suitable method, including image analysis, whereby a therapeutic composite is dried and imaged using a scanning electron micrograph (SEM). The amniotic membrane derived particles may have an irregular shape and in some embodiments are planar having a first planar surface and a second planar surface. Cryo-fracturing of amniotic membrane with a blunt object provides particles with less shear and a more irregular shape than conventional cryo-milling, thereby providing a higher surface area and more effective therapeutic effect.

The concentration of particles, such as micronized amniotic membrane, in the therapeutic composition and or fluid component may be provided in any effective amount such as more than about 0.1%, more than about 0.5%, more than about 1%, more than about 10%, more than about 25%, more than about 50%, more than about 75% or more than about 90% by weight of therapeutic composition and any range between and including the weight percentages listed. Likewise, the mass of particles, such as amniotic membrane particles, may be provided in a therapeutic fluid component of a therapeutic composition in any effective amount, such as more than about 1 mg/ml, more than about 5 mg/ml, more than about 10 mg/ml, more than about 50 mg/ml, more than about 100 mg/ml, more than about 500 mg/ml, and any range between and including the mass concentrations provided. The particles in the therapeutic composition may comprise collagen, growth factors, stem cells, amniotic stem cells, mesenchymal stem cells, progenitor cells, red blood cells, white blood cells, proteins, fibroblasts, paratenacytes, keratinocytes and the like.

An exemplary therapeutic composition may comprise an oxygen-carrier component that may increase the effectiveness of the therapeutic composite by increasing oxygen availability and increase stem cell viability. Any suitable oxygen-carrier component or combination of components may be included into a therapeutic compositing including, but not limited to, perfluorocarbon such as perfluorotributylamine (PFTBA), perfluorooctylbromide (PFOB), perfluorodecylbromide, perfluoroperhyclrophenanthrene and the like. An oxygen-carrier may be bonded, such as covalently bonded to a therapeutic composition, such as to a matrix component or to the micronized amniotic membrane. In one embodiment, a matrix component comprises a polymeric material, such a fluoropolymer, and an oxygen component is bonded thereto. Any suitable means may be used to bond an oxygen component to a therapeutic composition component including, cross-linking agents, radiation, and the like. In still another embodiment, an oxygen-carrier component may form an emulsion, or microemulsion with another fluid component. A perfluorocarbon oxygen-carrier component is hydrophobic and when mixed with a fluid component that is hydrophilic or comprises water, an emulsion may be formed comprising an aqueous phase and a perfluorocarbon phase.

Any of the fluid components described herein may be an injectable solution that will pass through a 20-gauge needle or a needle having a smaller diameter. In other embodiments, a fluid component is provided in a thicker composition, such as a paste that may be applied topically. The viscosity of an injectable fluid component may be no more than about 1 mPa sec, no more than about 500 mPa sec, no more than about 1000 mPa sec, no more than 20,000 mPa sec, no more than 50,000 mPa sec. In other embodiments, a fluid component may be provided for topical applications and the viscosity may be more than about 20 Pa sec, more than about 50 Pa sec, more than about 100 Pa sec, more than about 250 Pa sec and any range between and including the viscosity values provided.

In an exemplary embodiment, a therapeutic composition is a therapeutic composite and comprises any of the fluid components, as described herein, imbibed into or coated onto, a matrix component. A matrix component is a sheet, block, tube or rod of material, for example, that may comprises porosity and pores for accepting a fluid component therein. A matrix component may be a biological material such as an amniotic membrane. In another embodiment, an amniotic membrane may be provided as a matrix component in a multilayered configuration or combined with any other suitable support layer for a desired application. For example, a therapeutic composite, as described herein, may comprise an amniotic membrane layer and a cover layer. A cover layer may be used to reduce the loss, wash-out, of a fluid component from the therapeutic composite. In another embodiment, the therapeutic composite comprises an amniotic membrane and a support layer, such as a polymer matrix material including, but not limited to, a bioresorbable or fluoropolymer membrane. A support layer may have a tensile break strength that is much greater, such as two times or more that of an amniotic membrane layer in a matrix component. In still another embodiment, a therapeutic composite comprises one or more layers of amniotic membrane that are tensilized, whereby an amniotic membrane has been stretched in one or more directions to increase strength and/or area of the membrane. An amniotic membrane may be cross-linked, and a cross-linked amniotic membrane may be combined with a non-cross-linked amniotic membrane. Any suitable method, as known in the art of cross-linking an amniotic membrane may be used including chemical, such as treatment with glutaraldehyde, radiation and the like. A therapeutic composite as described herein, may comprise anti-inflammatory nano-particles and/or statins, HMG-CoA reductase inhibitors to reduce inflation at a treatment location. An exemplary therapeutic composition, and in particular a fluid component, may comprise mannitol, saline, ringers lactate, vitamin B complex and the like.

A therapeutic composite, as described herein, may be provided with the therapeutic fluid imbibed into, coated onto, or otherwise applied to a matrix component. For example, a therapeutic composite comprising an amniotic membrane may be provided with a therapeutic fluid component comprising micronized amniotic membrane particles dispersed in fluid component. This carrier fluid may be an amniotic stem cell concentrated fluid component. In an exemplary embodiment, the therapeutic fluid component and the amniotic membrane are from a single donor. In an exemplary embodiment, the amniotic membrane, the micronized amniotic membrane particles and the amniotic stem cells in the fluid component are all from a single donor. In another exemplary embodiment, a therapeutic composite comprises an amniotic membrane layer configured for direct application to a treatment location, a cover layer of a bioresorbable material and a therapeutic fluid component comprising a high concentration of amniotic stem cells. A portion of a bioresorbable material or other matrix layer of the therapeutic composite may be porous to enable a portion of the fluid component to be retained therein. Any suitable number and type of matrix or support layers may be configured in a therapeutic composite, as described herein. In one embodiment, a fluid component may be vacuum imbibed into a matrix component. Whereby a matrix component is submerged in a fluid component and vacuum is applied to remove substantially all the air from the matrix component. This removal of air will allow the fluid component to more substantially fill the voids and porosity of the matrix component.

A support layer may comprise any suitable type of material including, but not limited to, a bioresorbable material, a non-bioresorbable polymer material, such a polyether ether keton (PEEK), or polytetrafluoroethylene (PTFE), fluorinated ethylene propylene (PEP), perfluoroalkoxy (PFA) and the like, or a metallic component, such as stainless steel, titanium, gold and the like. A support layer may be porous and/or permeable. A support layer may be a membrane having a microstructure of pores, or a film, net, screen, woven and the like. A support layer may be substantially non-permeable to fluid and may be hydrophobic or oleophobic on at least one side. In an exemplary embodiment, a support layer is expanded PTFE. In an exemplary embodiment, a support layer is a sheet of material having a first substantially planar surface, a second substantially planar surface and a thickness.

A therapeutic composition may be introduced to a treatment location by direct topical application, such as by coating, applying, spraying, or placing over a treatment location and in some cases adhering a portion of the therapeutic composition with an adhesive, staples or sutures. In other embodiments, a therapeutic composition is delivered transcatheter and may be configured on any suitable implantable or delivery device, such as a slant or a deployable and removable balloon. In some embodiments, the fluid component, as described herein, is applied to the treatment location with both the matrix component and fluid component combined in a single step, whereby the fluid component is imbibed, coated or otherwise combined with the matrix component. In other embodiments, a matrix component is applied to a treatment location and a fluid component is subsequently added, such as by injection or topical application. For example, an amniotic membrane may be applied to a treatment location and a fluid component may subsequently be injected into the amniotic membrane and/or to the tissue under or around the location of the amniotic membrane. In still another embodiment, a first matrix component layer may be located on a treatment location and a second matrix component layer may be applied over the first matrix component layer. The first and/or second layer may comprise a fluid component and each layer may comprise a different composition of fluid component. A second matrix component layer may be substantially non-permeable to the fluid component thereby reducing wash-out or dilution of the fluid component from bodily fluid exposure.

A therapeutic composition, as described herein, comprises other biological materials that are not amnion derived. In one embodiment, a therapeutic composition comprises a stromal vascular fraction (SVF) from a patient that is to be treated with the therapeutic composition. Stromal vascular fraction derived from adipose tissue of a patient, for example, may be combined with the matrix and/or fluid component as described herein. In an exemplary embodiment, stromal vascular fraction is combined with micronized amniotic membrane and/or amniotic stem cells to form a fluid component. In another embodiment, a stromal vascular fraction is combined with a matrix component either before or after locating the matrix component over the treatment location. The stromal vascular fraction may contain any of the following: preadipocytes, mesenchymal stem cells (MSC), endothelial progenitor cells, T cells, B cells and mast cells as well as adipose tissue macrophages. In another embodiment, a therapeutic composition comprises bone marrow aspirate (BMA) and/or platelet rich plasma (PRP).

The therapeutic composition, as described herein, may be cryopreserved whereby the temperature of the therapeutic composite is lowered to a temperature of no more than −70° C., and preferable lower than about −80° C. The rate of cooling may be controlled to reduce damage and maintain viability of the cells upon thawing.

As shown in Table 1 below, an exemplary fluid component comprising a concentrated amniotic stem cell fluid and micronized amniotic membrane particles, as described in Example 1, retained a very high viability post controlled rate freezing. Maintaining the amniotic membrane in a hydrated state prior to cryo-fracturing and subsequent cryopreserving improves cell viability.

TABLE 1

| Donor | Cell Viability Prior to Controlled Rate Freezing | | Cell Viability Post Controlled Rate Freezing | |
|---|---|---|---|---|
| 1 | Sample 1 | 98.4% | Sample 1 | 93.1% |
|   | Sample 2 | 98.5% | Sample 2 | 90.0% |
|   | Sample 3 | 98.1% | Sample 3 | 90.9% |
| 2 | Sample 1 | 97.3% | Sample 1 | 93.1% |
|   | Sample 2 | 97.5% | Sample 2 | 91.3% |
|   | Sample 3 | 94.7% | Sample 3 | 92.5% |
| 3 | Sample 1 | 95.6% | Sample 1 | 92.5% |
|   | Sample 2 | 95.1% | Sample 2 | 95.5% |
|   | Sample 3 | 94.6% | Sample 3 | 92.5% |

The viability of cells was maintained after thawing a cryo-preserved concentrated amniotic fluid as reported in Table 1. A small loss in viability was observed with a total viability after thawing a cryopreserved therapeutic composite of more than 90% in all cases. A therapeutic composite, as described herein, may have a cell viability of about 70% or more, at least about 80% or more, about 90% or more and any range between and including the cell viability values provided.

Any of the therapeutic compositions described herein may be used for a wide variety of treatment applications. A therapeutic composition, as described herein, may be provided to any suitable treatment location of the body to induce an immunomodulatory and/or anti-inflammatory response. In another application, a therapeutic composition is introduced into a treatment location to reduce scaring and to promote healing, whereby the therapeutic composition aids in regeneration of new tissue. A fluid component of the therapeutic composition, as described herein, may be injected directly into an affected area, introduced intravenously, through shunts, or ports. It may be desirable to provide a fluid component comprising both amniotic stem cells and micronized amniotic membrane when tissue, regeneration is desired. The micronized amniotic membrane particles may provide the architecture needed for more effective regeneration and tissue repair.

A therapeutic composition, as described herein, may be introduced into any organ of the body including, but not limited to, the heart, brain, lung, liver, kidney, pancreas, stomach, intestine and the like through transcatheter, or topical application. In some embodiment, a therapeutic composition, as described herein is configured onto a stent or is positioned by a balloon catheter.

A therapeutic composition may be used to treat any number of heart related conditions, including, but not limited to, restrictive and constrictive cardiomyopathy, ischemic cardiomyopathy, idiopathic cardiomyopathy, allograft vasculopathy, atherosclerosis, arrhythmia, post-operative atrial fibrillation, hypertension, pericarditis, indocarditis, myocarditis, acute myocardial infraction, carotid endarterectomy, chronic heart failure with scare, heart failure with low ejection fraction less than 35%, coronary artery disease with regional wall abnormalities, post-operative heart recovery and scaring and infective endocarditis. Post-operative atrial fibrillation may be treated with by placement of the therapeutic composition on the epicardium. In another embodiment, a therapeutic composition is used to treat a valve and/or leaflet defect. A therapeutic composition may be used to regenerate a portion of a valve or leaflet, for example. Treatment of these heart conditions may include introduction of a therapeutic composition, as described herein, to a heart by topical application to a portion of a heart or epicardium for example, inter-arterially, intravenously, intra-arterially including intrarenal, intracoronary and intra-carotid, and/or trans-bronchially. In one embodiment, a therapeutic composition comprising a matrix component is applied directly to the heart or vascular portion of the anatomy and attached by adhesive, sutures or staples, for example. In another embodiment, a therapeutic composition is wrapped around a portion of an artery or vein and may be adhered to itself to retain the therapeutic composition in place. For example, a therapeutic composition may be wrapped around the carotid artery in an endarterectomy procedure before or after suturing the carotid artery.

An exemplary method of treating a heart includes applying a therapeutic composition, as, described herein after the concluding portion of a coronary bypass graft surgery (CABG) and after the grafts are completed. A therapeutic composition comprising an amniotic membrane matrix component, may be attached to the retracted pericardium or on the myocardium. A therapeutic matrix component may be attached to the heart with any suitable adhesive, sutured thereon, or held in place by hydrostatic tension. A matrix component attached to a portion of the heart may comprise a fluid component, containing, micronized amnion membrane that includes a multitude of growth factors such as, insulin, or growth factor 1, transforming growth factor b1, cytokine proteins, collagen substrates, extracellular matrix proteins such as laminin, fibronectin, annexin, vitronectin and the like. These components may produce a therapeutic effect on the heart, or the myocardium and reduce inflammation, prevent scarring and fibrosis. The effect of anti-inflammation, and anti-fibrosis, have been found to have a profound positive effect on the electrical activity function of the heart (myocardium). An effective does of fluid component may be provided in one treatment or in several doses over a period of time. The specific treatment and dosing regime will depend on the type and severity of the condition to be treated.

A study evaluating the therapeutic effectiveness of applying a therapeutic composition, as described herein is described in the American Journal of Medicine, Vol 128, No. 1, "First in Man: Amniotic Patch Reduces Postoperative Inflammation", by Dr. Zain Khalpey, at al; the entirety of which is incorporated by reference herein.

Stents are known to be configured for almost every portion of the vascular system and are becoming smaller and more versatile in their applications. Cardiac stents, thoracic aortic stents, abdominal aortic stents, coronary stents, endoprosthesis and any other stent for the vascular system may be configured with a therapeutic composition, as described herein. A matrix component may be configured around an exterior portion of the stent to provide better adhesion to the treatment location.

In one embodiment, a fluid component is injected into a specific treatment location through the use of a catheter, such as a steerable catheter and an injection implement configured on the introductory end of the catheter. For example, a catheter having an injection implement may be introduce into the femoral artery, inserted to position the injection implement in proximity to the heart, whereby a dose of therapeutic composite is administered into the tissue of the heart.

A therapeutic composite, as described herein, may be used to treat any number of orthopedic conditions including, but not limited to, chondral defects, articular cartilage defects, arthritis, osteoarthritis, osteochondral defects or injuries, cartridge and tendon wear, tear and injury, tendinopathahies, i.e., tendonitis and tendinosis, and the like. For example, a therapeutic composite may be used to treat any Berndt & Hardy grading of osteochondritis dessicans, from undisplaced, partially detached, detached but not displace and detached and displaced or rotated. A therapeutic composite, as described herein, may be introduced to a joint, bone, tendon or cartilage to induce an immunomodulatory and/or anti-inflammatory response. The therapeutic composite may be placed surgically or arthroscopically into an affected area, such as a joint, bursa, synovial membrane, synovium, intra articular, cartilage, tendon or between the tendon and partenon. In an exemplary embodiment, the therapeutic composite is introduced arthroscopically, or by small arthrotomy. The matrix component may be wrapped around a tendon with a defect, such as a tear, and the fluid component, as describe herein, may be injecting into or otherwise applied to the matrix component, prior to or after location of the matrix component on the tendon. A matrix component may be applied to a damaged or thinned area of cartilage or fractured, partially broken osteochondral injury, and subsequently the fluid component, as described herein may be applied to the matrix material. A matrix component may be imbibed with and or coated with a fluid component as described herein prior to positioning the therapeutic composite on a treatment location.

A therapeutic composite, as described herein, may be used to treat any number of skin conditions and/or injuries including, but not limited to, keloid scaring, cuts, abrasions, infections, boils, surgical incisions and/or tumor removal, psoriasis, plastic surgery and the like. A therapeutic composite, as described herein, may be introduced into to treatment location to promote tissue regeneration and to reduce scarring. In one embodiment, a therapeutic composite is placed over an operative incision upon closure of the incision and may be place on the interior surface of the incision, and/or the exterior of the incision. Again, the inner wall of the incision may be treated with a therapeutic composite that incorporates both a matrix component and a fluid component, as described herein. The therapeutic composite may be antifibrotic and thereby reduce scarring.

In one embodiment, a therapeutic composition is used to treat keloids by application of a therapeutic fluid to the keloid scar intralesionally and/or subcutaneous to the keloid scar. Application of the therapeutic fluid may be provided periodically to reduce the size and severity of the keloid scar through tissue regeneration and reformation. Any suitable dose of therapeutic fluid, as described herein may be used to treat a keloid scar.

A therapeutic composition may be used to in breast reconstruction, or any plastic surgical repair. Strips of a therapeutic matrix component may be applied along exposed organs, nerves, and fascial planes. Typically, hydrostatic tension will hold the matrix component in place. However, in some anatomic locations, hydrostatic tension may not provide sufficient adhesion. A surgical glue or sutures may be used to retain the matrix component in position.

A therapeutic composition, as described herein, may be used to treat a nerve injury through injection of a therapeutic fluid in close proximity to a damaged nerve or through application of a matrix component to an exposed nerve, through surgery. A nerve may be exposed configured in a proper anatomic alignment and a matrix component may be configured around the damaged nerve to form a tunnel. Subsequently, a fluid component may be injection into the matrix component or into surrounding tissue. In one embodiment, a pudendal nerve may be treated with a therapeutic composition after prostrate surgery, for example.

therapeutic composite, as described herein, may be used to treat digestive system conditions including application to reduce scarring of operative procedures including a stomach reduction or stomach by-pass surgery and to prevent intestinal strictures.

A therapeutic composite, as described herein, may be used to treat reduce scarring post plastic surgery, whereby the therapeutic composite is placed on the inside surface of the dermal tissue to reduce scarring. For example, when an incision is made in the abdomen, a therapeutic composite may be placed on the interior of the abdominal wall before closure of the incision.

A therapeutic composition as described herein may be used to treat burns, including second and third degree burns. A therapeutic composition, as described herein, may be applied over a burn location to reduce post burn scarring and to accelerate dermis and epidermal regeneration. A therapeutic fluid, or fluid component, as described herein, may be injected into and/or around a burn location. An exemplary fluid component for treatment of burns comprises amniotic fluid and micronized amniotic membrane, such as 1 ml of fluid per about 8 cm2 of micronized amniotic membrane. In an exemplary embodiment, injections of a fluid component are made around a burn location and a matrix component of amniotic membrane is placed over the burn. The amniotic membrane may comprise a therapeutic component, whereby the membrane is imbibed with or coated with a fluid component before application to the burn location. In an alternative embodiment, a fluid component may be sprayed onto the burn location with care being taken to prevent leaking or run-off of the fluid component from the burn location. A dressing may be positioned around the burn prior to spraying to catch any run-off. A fluid component may be applied to a burn, such as my injection or spraying, subsequent to the initial treatment. The severity of the burn or wound and the response of the patient to the treatment may dictated the time interval(s) for additional application of fluid component.

A venous stasis wound may be treated by the application of a matrix component comprising amniotic membrane and/or the application of a fluid component through injection, spraying and/or coating on the matrix component.

A therapeutic composite, as described herein, may be used to induce an immunomodulatory and/or anti-inflammatory response in an eye. For example, a therapeutic composite may be used to reduce scaring and promote healing by application to the cornea. A fluid component may be applied periodically to a matrix component that is located on a portion of an eye. In addition, fluid component may be vacuum imbibed into a matrix component to produce a more transparent therapeutic composite. Vacuum imbibing of a fluid component into a matrix component may greatly increase light transmission as many matrix components, including amniotic membranes are typically translucent.

A therapeutic composition, as described herein, may be used to treat muscle tears or muscle traumatic loss. An inflammatory signal may be created by needling techniques, use of infrared diode laser, radial pulse generator to the area, extra corporeal shockwave i.e. dornier epos, epat device or surgical repair. Therapeutic fluid may be administered by injection into the muscle treatment location. A second dose or treatments may be applied in approximately four to six weeks depending on patient response and recover.

A therapeutic composition, may be used to treat chronic tendiopathy, fasciopathy, and the like. Ultrasound imaging may be used to diagnosis the condition and to better understand the microvascular architecture of the tendon to be treated. An inflammatory signal may be created as described herein. Therapeutic fluid may be administered using ultrasound guidance around the paratenon of the injured tendon or fascia. Non-steroidal medications, steroid medications, and/or disease modifying medications may be discontinued. A second dose or treatments may be applied in approximately four to six weeks depending on patient response and recover.

A therapeutic composite, as described herein, may be used equine conditions including tendinitis, tendinosis, tendinopathy, osteoarthritis, laminitis. A therapeutic composite may be used any of the ways described herein.

An effective dose of fluid component may be provided in one treatment or in several doses over a period of time. The specific treatment and dosing regimen will depend on the type and severity of the condition to be treated. An initial dose of fluid component may be provided with a matrix component upon initial application of the matrix component to the treatment location. Subsequent doses of fluid component may be administered thereafter as required, and may be applied topically, Such as in wound applications, or through injection, such as in deep applications. In one embodiment, a fluid component is injected into a specific treatment location through the use of a catheter, such as a steerable catheter and an injection implement configured on the introductory end of the catheter.

A therapeutic composition, as described herein, may be introduced into any organ of the body including, but not limited to, the heart, brain, lung, liver, kidney, pancreas, stomach, intestine and the like through transcatheter, direct injection, or topical application. In some embodiment, a therapeutic composition, as described herein is configured onto a stent or is positioned by a balloon catheter, in another embodiment, a therapeutic composition comprising a matrix component is configured onto a treatment location and in some cases may be wrapped around a tubular anatomical body portion, such as an intestine, ureter, urethra, fallopian tubes, vas deferens and the like. A matrix component may be wrapped around the tubular body part during a surgical procedure or through the use of orthoscopic procedures.

A therapeutic composition, as described herein, may be used to treat urology conditions including post-operative scarring and strictures, for example. Strictures in the ureter and urethra may be treated by placement of a therapeutic composite to a stricture location to reduce scarring and blockage of the ureter. Stricture treatment may comprise configuring a therapeutic composite around at least a portion of the ureter or urethra. In some embodiments, a therapeutic composite is wrapped completely around a ureter or urethra.

A therapeutic fluid, as described herein, may be provided intravenously to regulate systemic immune modulation post-surgery. An exemplary therapeutic fluid may comprise mannitol, saline, ringers lactate, vitamin B complex and the like. Mannitol may be incorporated into therapeutic compositions for introduction into the brain, as the mannitol may help the treatment composition to pass through the brain barrier.

A therapeutic composition may be used to treat any number of lung related conditions, including, but not limited to, lung fibrosis, chronic obstructive pulmonary disease (COPD), acute lung injury, transplanted lung rejection, pulmonary hypertension, ventilator induced lung injury, acute respiratory disease syndrome (ARDS), bronchitis, alveolitis, chronic parenchymal and pleural lung disease, trans-bronchial parenchymal disease, post-operative lung recovery and scaring and/or empyema. Treatment of these lung conditions may include introduction of a therapeutic composite, as described herein, to a lung by topical application to a portion of a lung, inter-arterially, intravenously into the venous portion of the circulatory system including the pulmonary artery, through a central venous catheter, peripheral venous catheter and the like.)

A therapeutic composite may be used to treat any number of brain related conditions, including, but not limited to, stroke, ischemic stroke, traumatic brain injury and post-operative brain recovery, gliobastorna, and scaring. Additional brain related conditions that may be treated with a therapeutic composition, as described herein include, but are not limited to, Parkinson's disease, autism, CVA's, TIA's depression, macular degeneration, dementia, neurofibromatosis, neuro degenerative diseases, Charcot-Marie-Tooth (CMT), multiple sclerosis, and other neuro degenerative diseases i.e. ALS and the like. Treatment of these brain conditions may include introduction of a therapeutic composite, as described herein, by placement during surgery to an affected area of the brain. In another embodiment, a therapeutic fluid is provided to a portion of the brain through IV infusion, intra-arterial infusion, through a shunt or any suitable port. In order to enable or increase the passage of the therapeutic fluid to the brain, mannitol may be incorporated into the fluid, along with saline in some cases.

A therapeutic composite may be used to treat any number of other organ related conditions including, but not limited to, diabetes, renal failure, kidney failure, post-operative kidney or liver recovery and scaring, and the like. Treatment of these conditions may include introduction of a therapeutic composite, as described herein, topically, by transcatheter and the like. An effective does of fluid component may be provided in one treatment or in several doses over a period of time. The specific treatment and dosing regime will depend on the type and severity of the condition to be treated.

A therapeutic composition comprising a therapeutic matrix component may be applied to any organ, or tissue for adhesion prevention. For example post an anastomosis or other operative procedure of a ureter, urethra, fallopian tubes, intestine or vas deferens, a matrix component may be applied over an effected area with or without a fluid component. Any anatomical body portion that can be constricted may have a matrix component, as described herein, wrapped around for the purpose of treatment after surgery, for example.

A therapeutic composition may be used to treat erectile dysfunction through injection of a therapeutic fluid into and around the base of the penis, such as in and around the neurovascular bundles to reduce vascular constriction. In addition, patients suffering from Peyronie's disease may be treated by injection to the affected area of the penis.

In one embodiment, a fluid component is injected into a specific treatment location through the use of a catheter, such as a steerable catheter and an injection implement configured on the introductory end of the catheter. For example, a catheter having an injection implement may be introduce into the femoral artery, inserted to position the injection implement in proximity to an organ, whereby a dose of therapeutic composite is administered into the organ.

A frozen dose of a therapeutic composition, as described herein may, be prepared, provided for use and utilized according to the teachings of PCT application no. PCT/US/ 2015035749, to Amnio Technolgy LLC, and entitled Frozen Therapeutic Dose and Packaging; the entirety of which is hereby incorporated by reference herein.

The summary of the invention is provided as a general introduction to some of the embodiments of the invention, and is not intended to be limiting. Additional example embodiments including variations and alternative configurations of the invention are provided herein.

BRIEF DESCRIPTION OF THE DRAWINGS

The accompanying drawings are included to provide a further understanding of the invention and are incorporated in and constitute a part of this specification, illustrate embodiments of the invention, and together with the description serve to explain the principles of the invention.

DETAILED DESCRIPTION OF THE ILLUSTRATED EMBODIMENTS

Figures 1A, 1B:
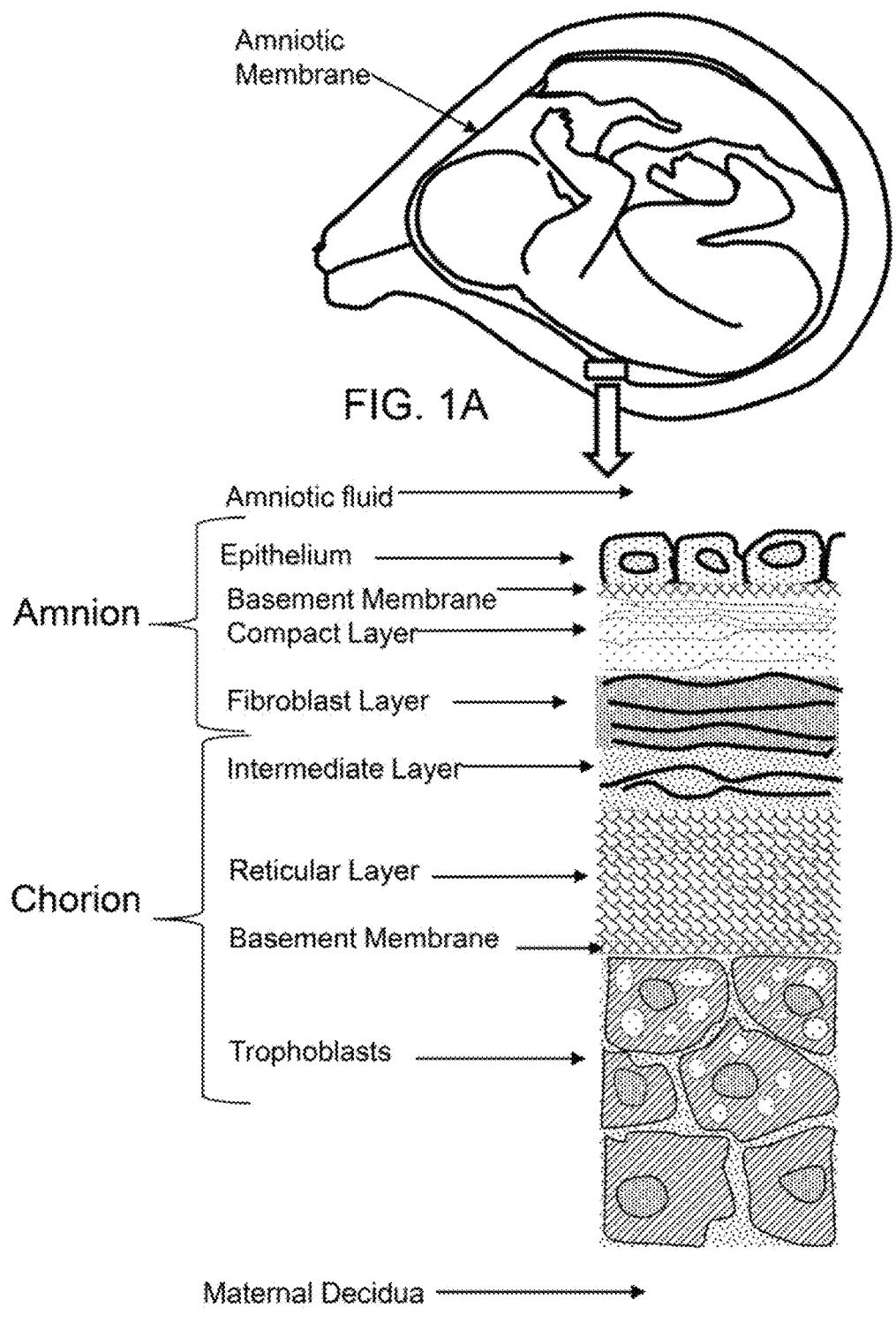

FIG. 1A shows a cross-sectional diagram of amniotic membrane surrounding a fetus in utero.

FIG. 1B shows a cross-section diagram of the layers of the amnion and chorion.

Figure 2A:
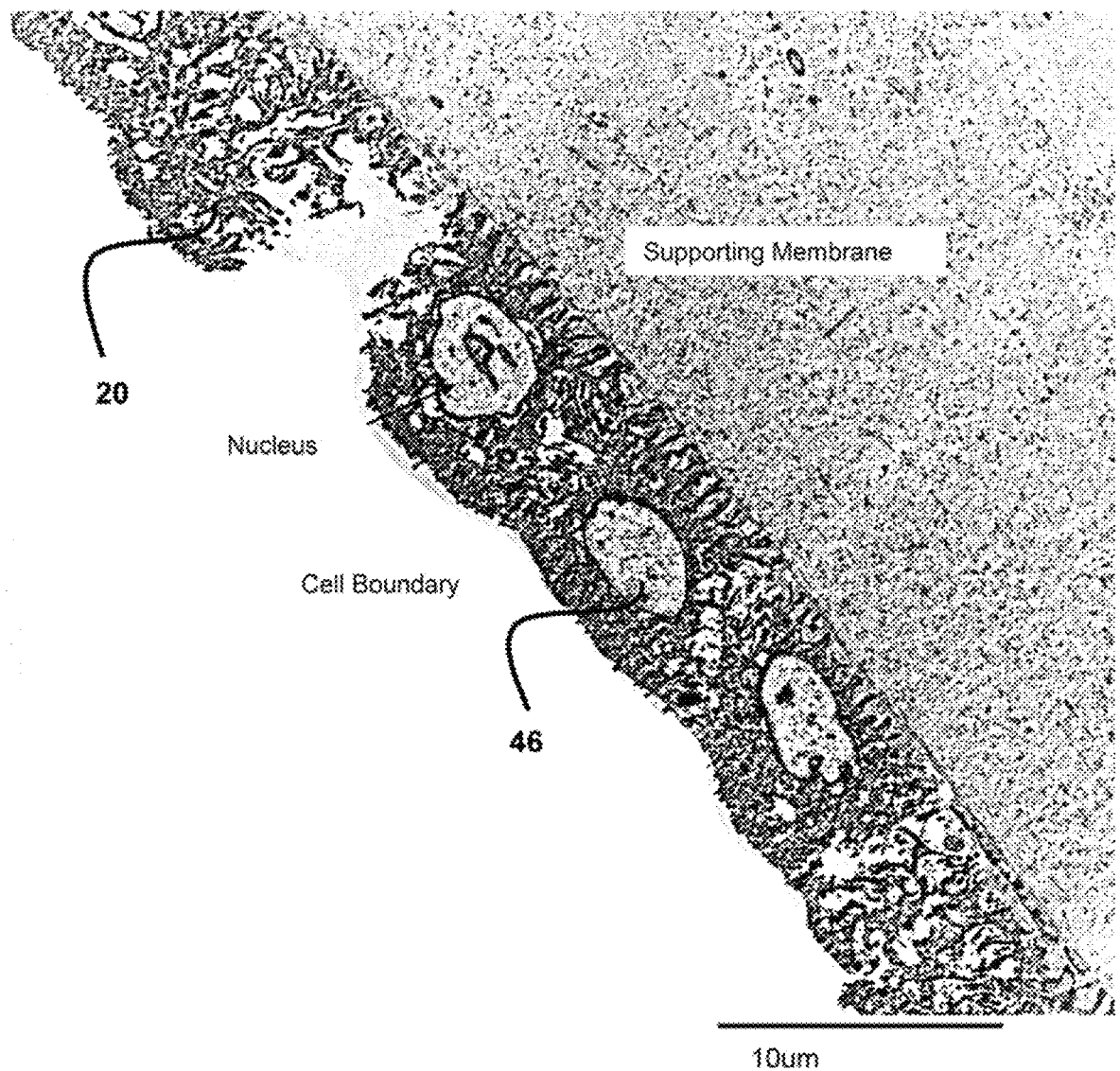

FIG. 2A show a transmission electron micrograph (TEM) of the epithelium layer of the amniotic membrane having a single layer of amniotic stem cells. The TEM is at 2500× magnification.

Figure 2B:
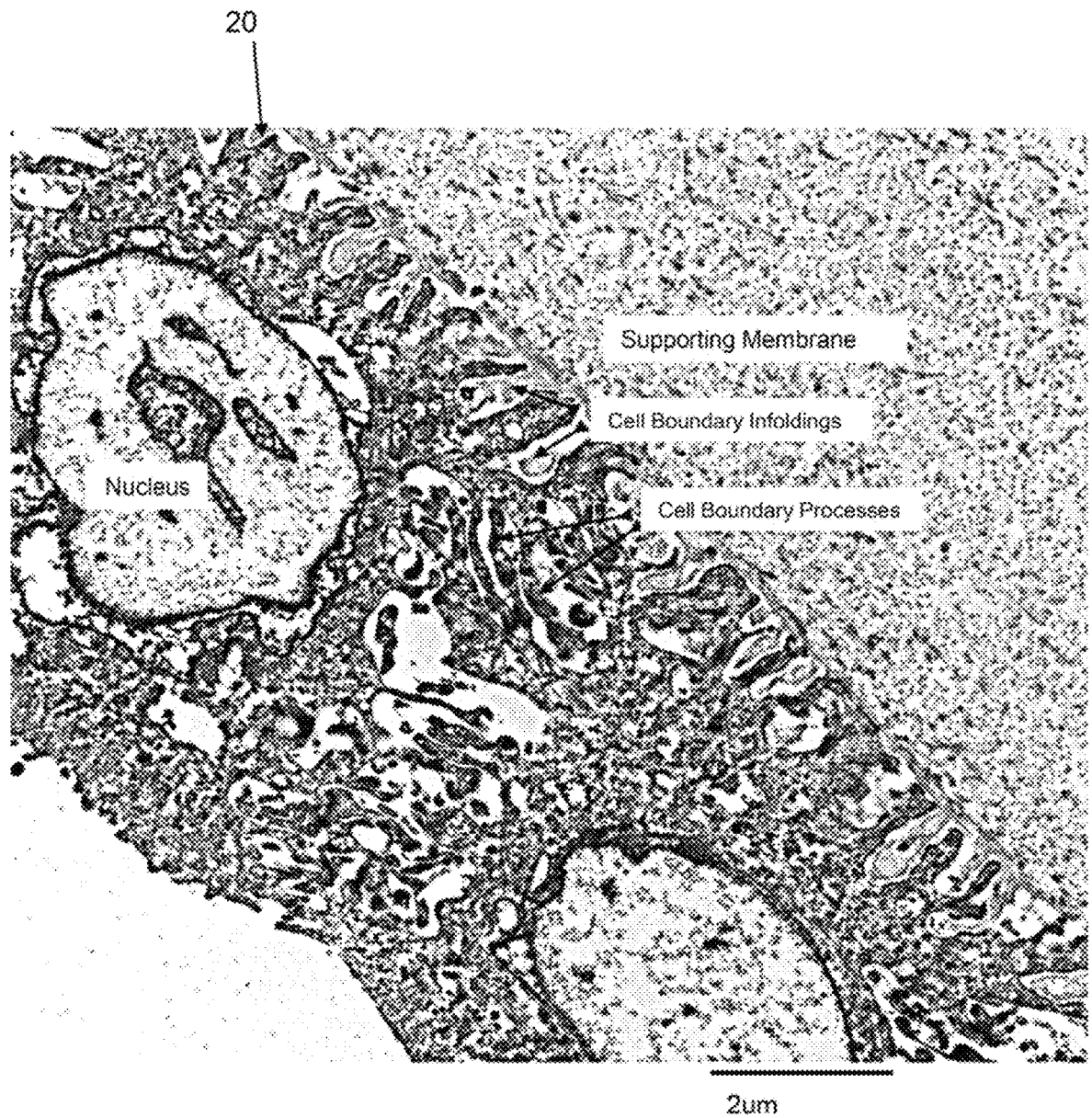

FIG. 2B show a TEM of the epithelium layer of the amniotic membrane having a single layer of amniotic stem cells. The TEM is at 8200× magnification.

Figure 3A:
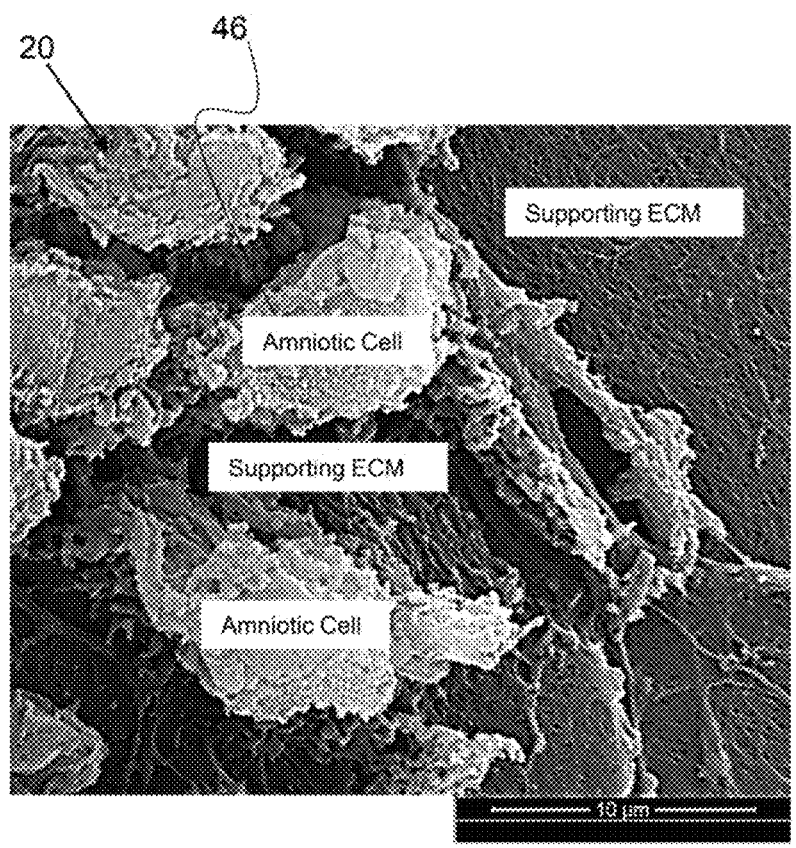

FIG. 3A is a scanning electron micrograph (SEM) of an amniotic membrane having amniotic stem cells.

Figure 3B:
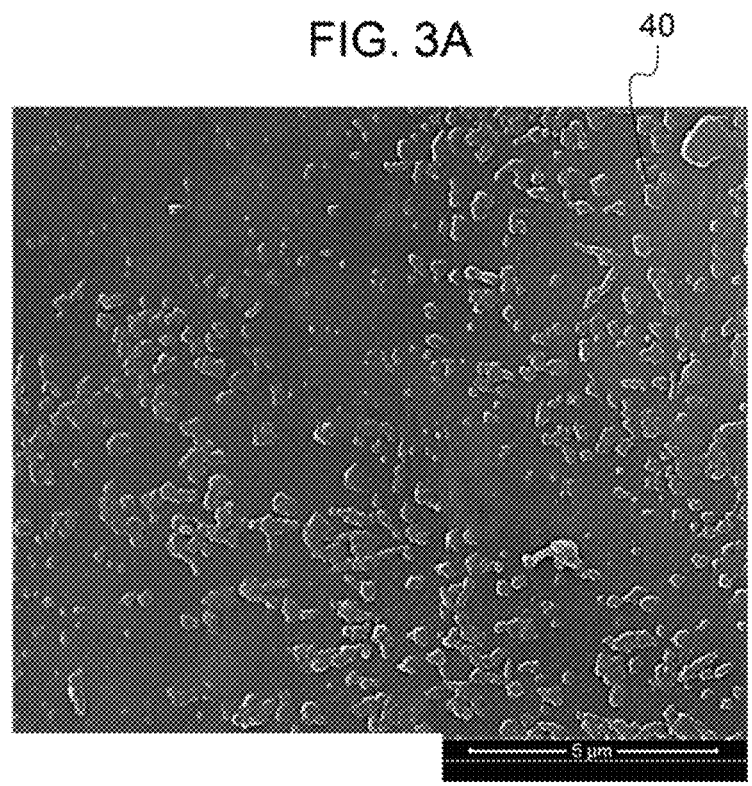

FIG. 3B is a SEM of cryo-fractured amniotic membrane particles.

Figure 4:
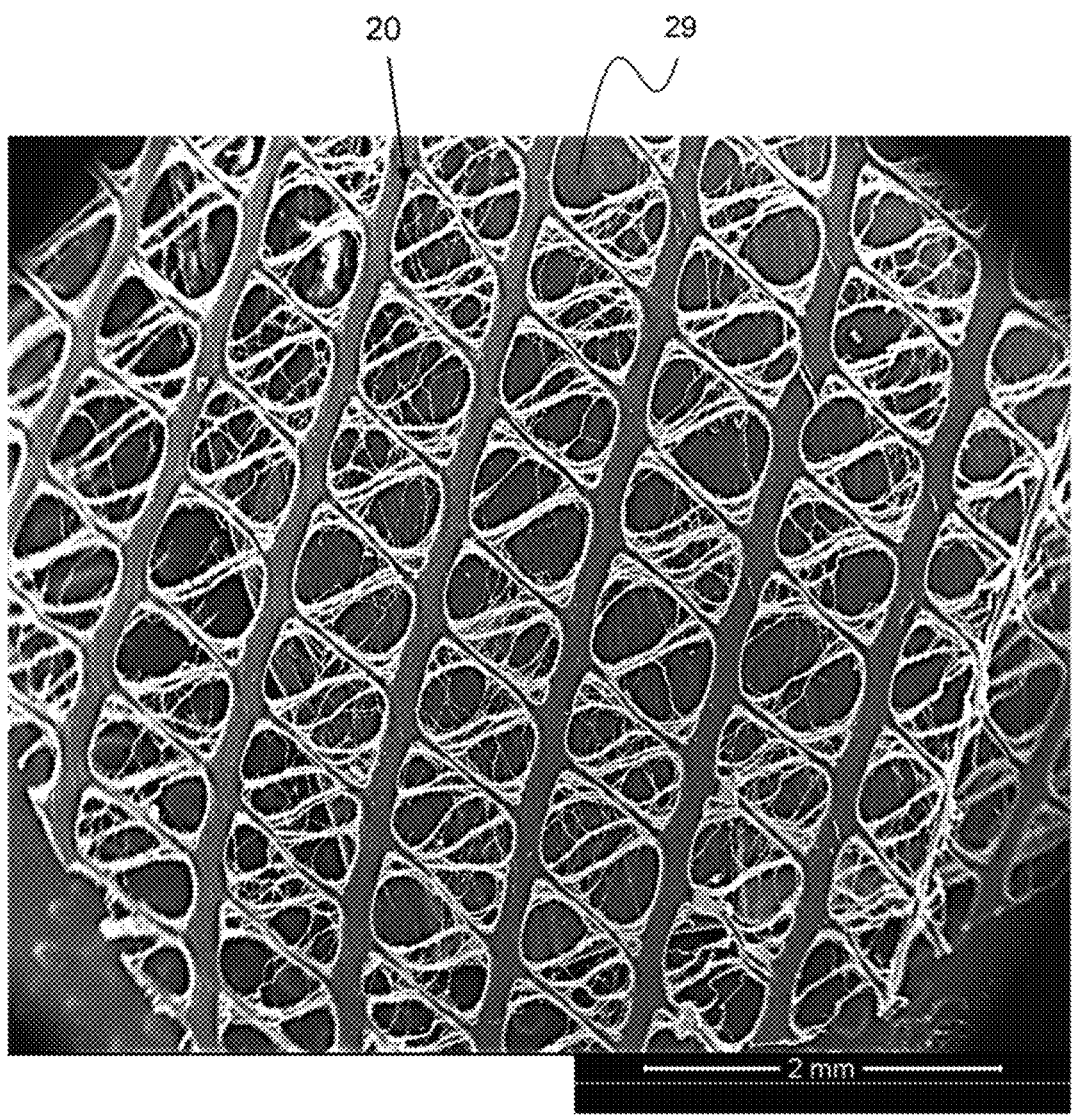

FIG. 4 is a scanning electron micrograph (SEM) of an amniotic membrane having pores between the amniotic membrane tissue.

Figure 5A:
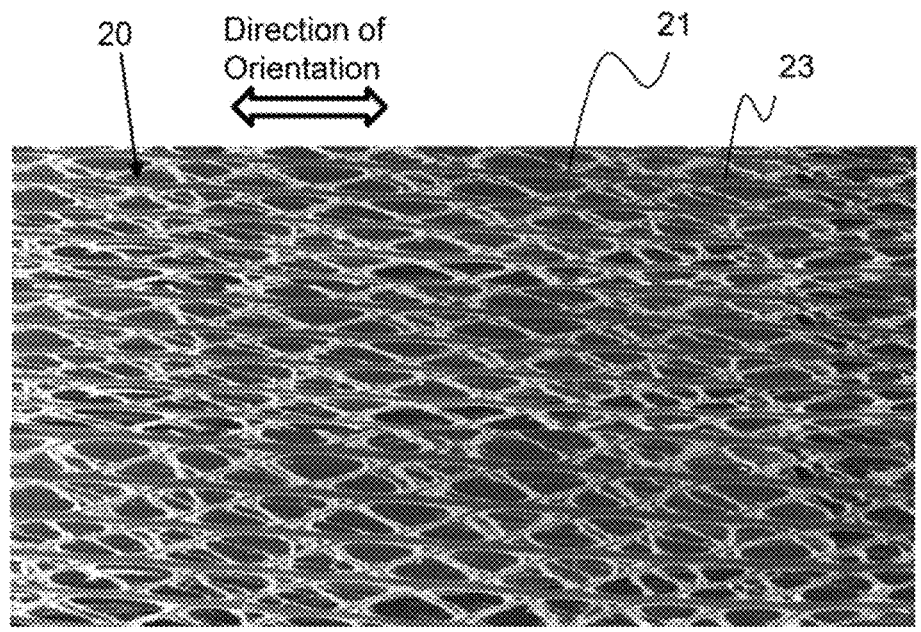

FIG. 5A is a representation of an exemplary tensilized amniotic membrane.

Figure 5B:
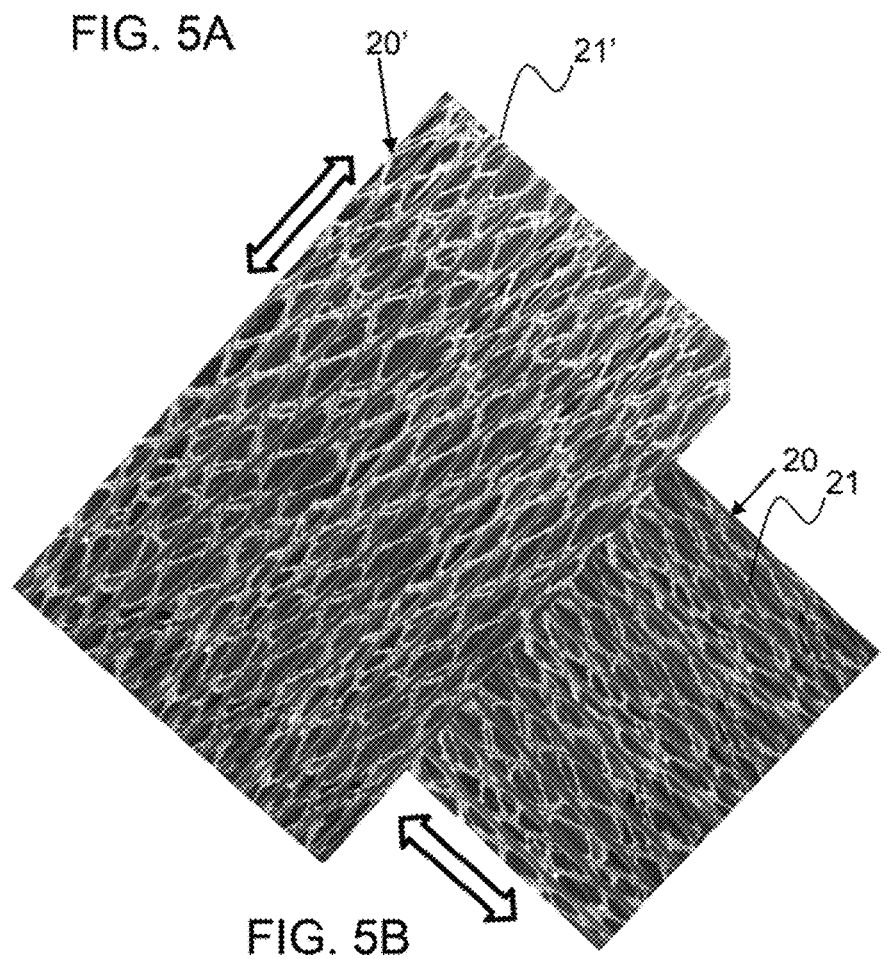

FIG. 5B is a representation of two exemplary tensilized amniotic membranes being layered together.

Figure 6:
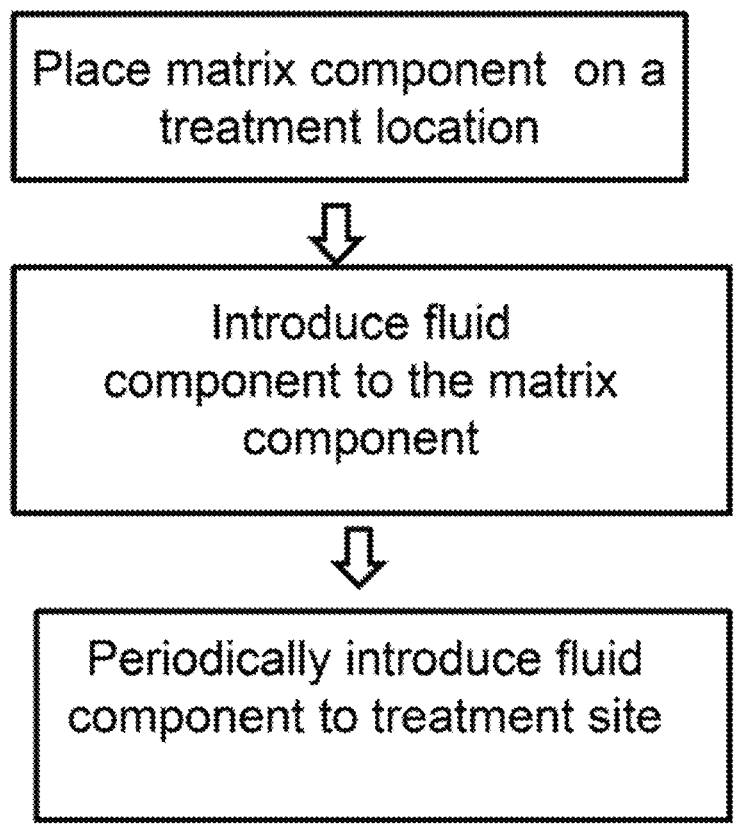

FIG. 6 shows a diagram of an exemplary method to apply a therapeutic composition, as described herein.

Figure 7:
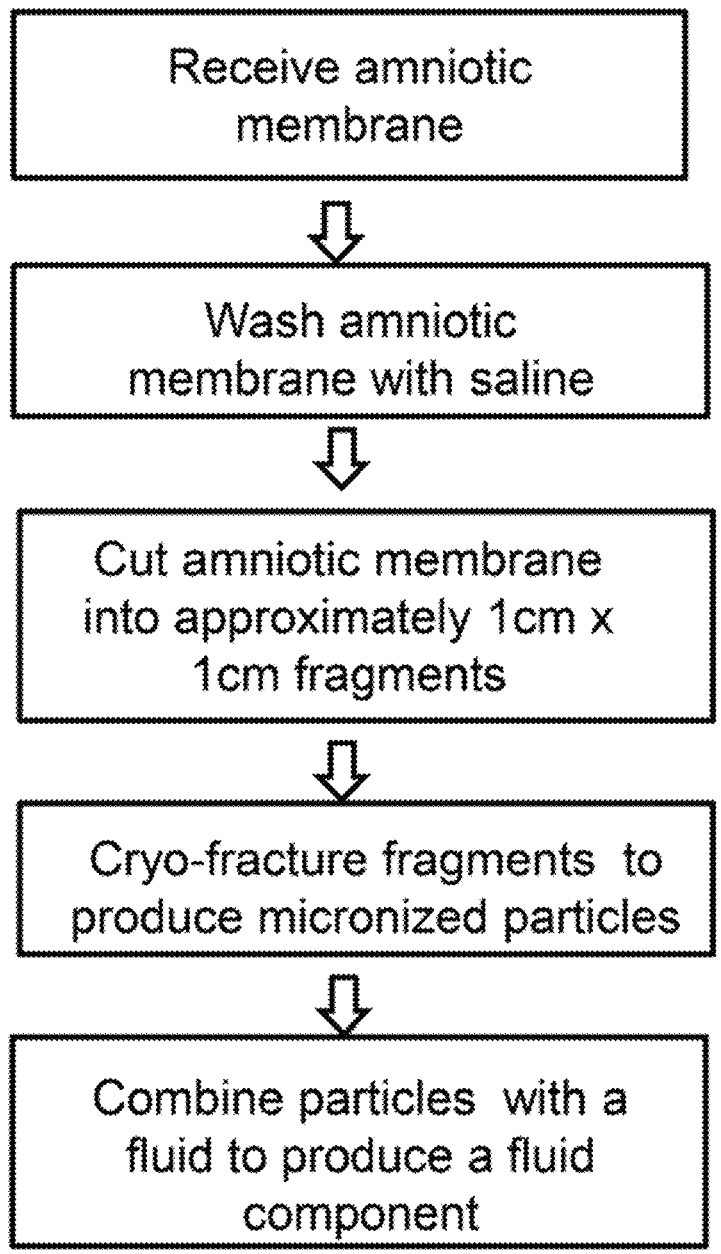

FIG. 7 shows a diagram of a process to produce a fluid component comprising micronized amniotic membrane particles.

Figure 8:
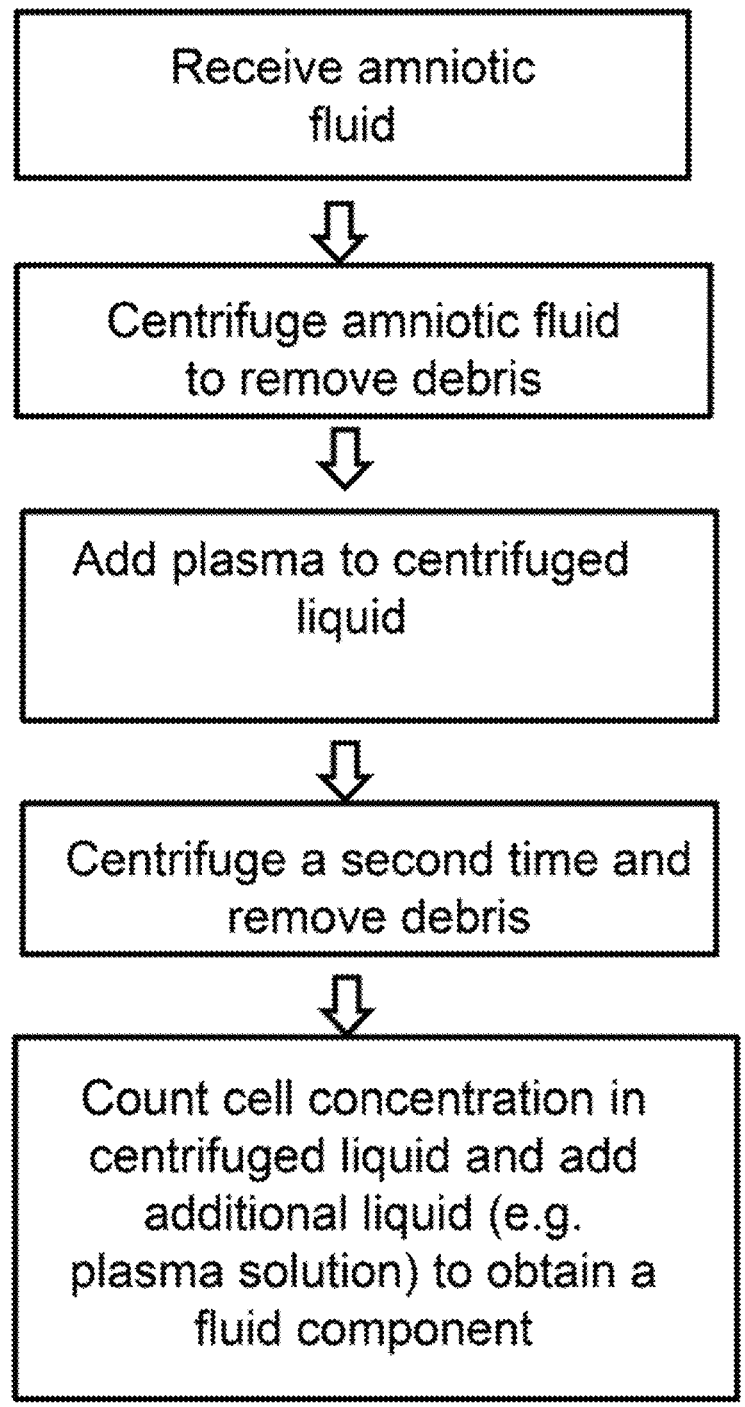

FIG. 8 shows a diagram of a process to produce a fluid component comprising a concentrated stem cell fluid.

Figure 9:
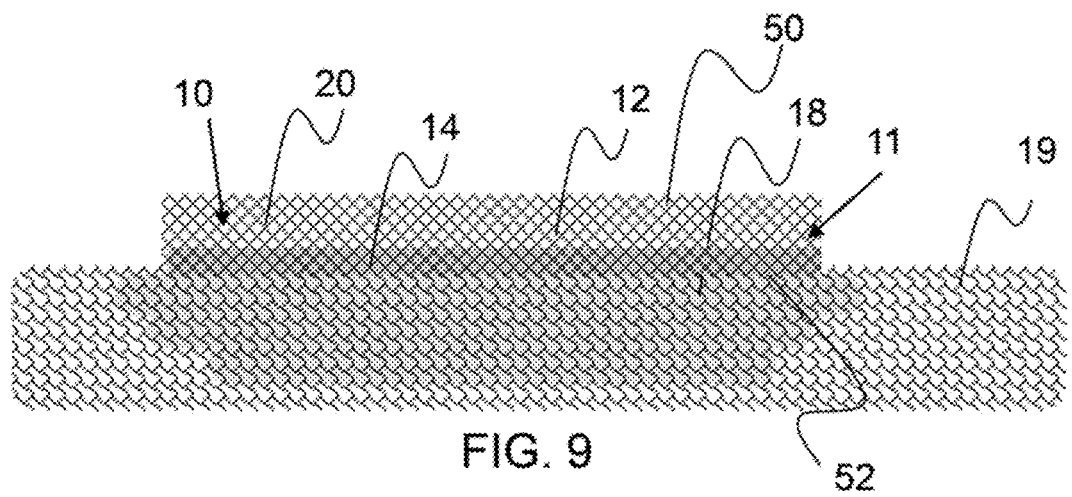

FIG. 9 shows a cross-sectional representation of an exemplary amniotic membrane configured over a treatment location.

Figure 10:
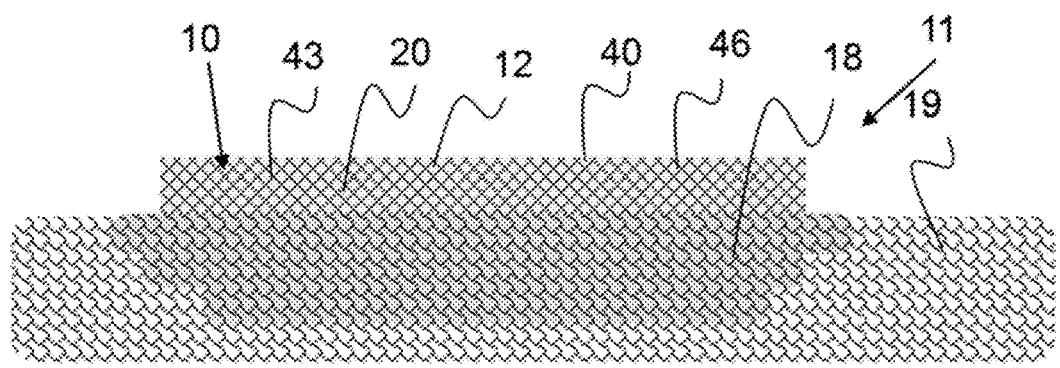

FIG. 10 shows a cross-sectional representation of an exemplary therapeutic composition comprising an amniotic membrane and fluid component configured over a treatment location.

Figure 11:
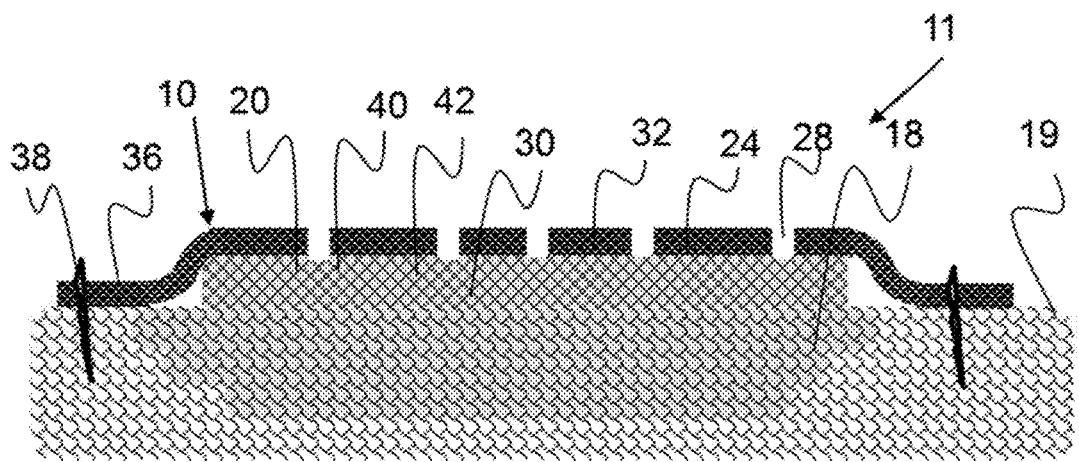

FIG. 11 shows a cross-sectional representation of an exemplary therapeutic composite configured over a treatment location wherein the therapeutic composition comprises an amniotic membrane matrix component imbibed with a fluid component and a cover layer configured there over.

Figure 12:
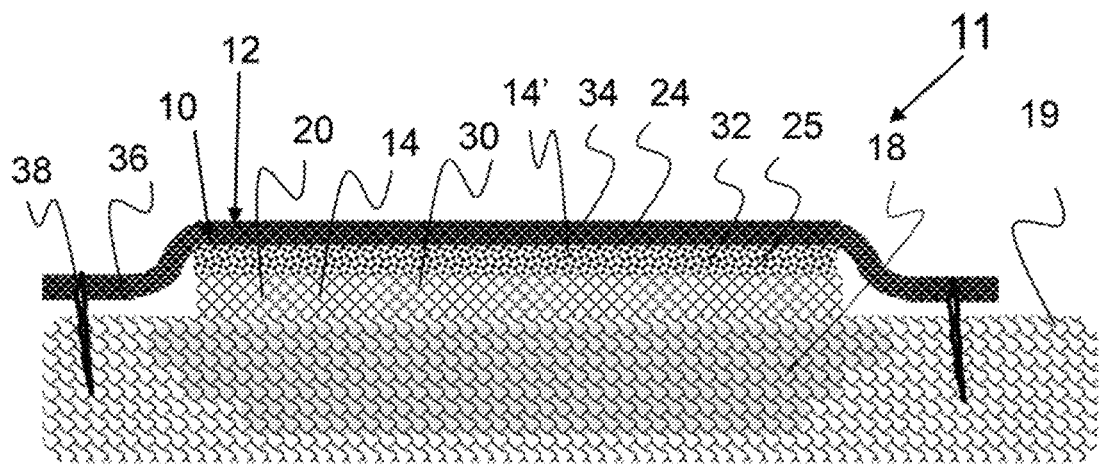

FIG. 12 shows a cross-sectional representation of an exemplary therapeutic composite configured over a treatment location wherein the therapeutic composite comprises a first matrix layer of amniotic membrane, a second matrix layer of a fluid component reservoir, and a third matrix layer that is a cover layer.

Figure 13:
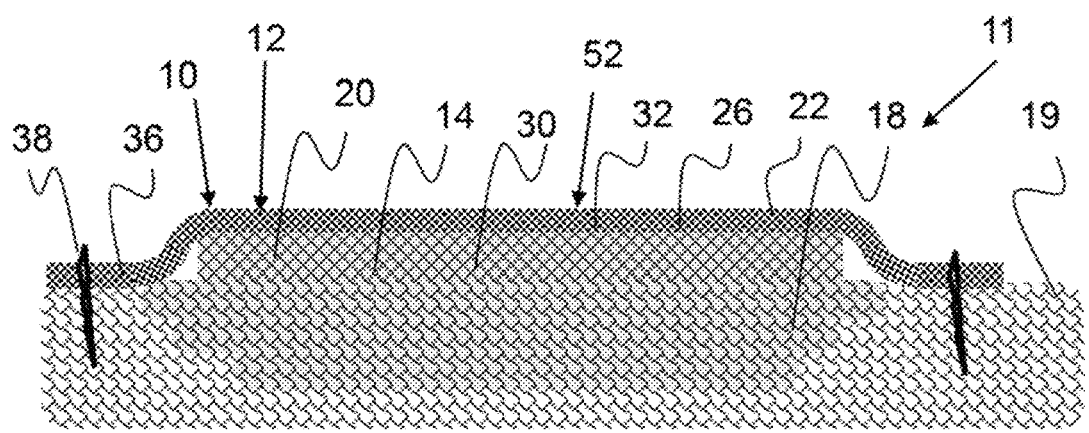

FIG. 13 shows a cross-sectional representation of an exemplary therapeutic composite configured over a treatment location wherein the therapeutic composite comprises a first matrix layer of amniotic membrane imbibed with fluid component and a second matrix layer that is a support layer comprising bioresorbable material.

Figure 14:
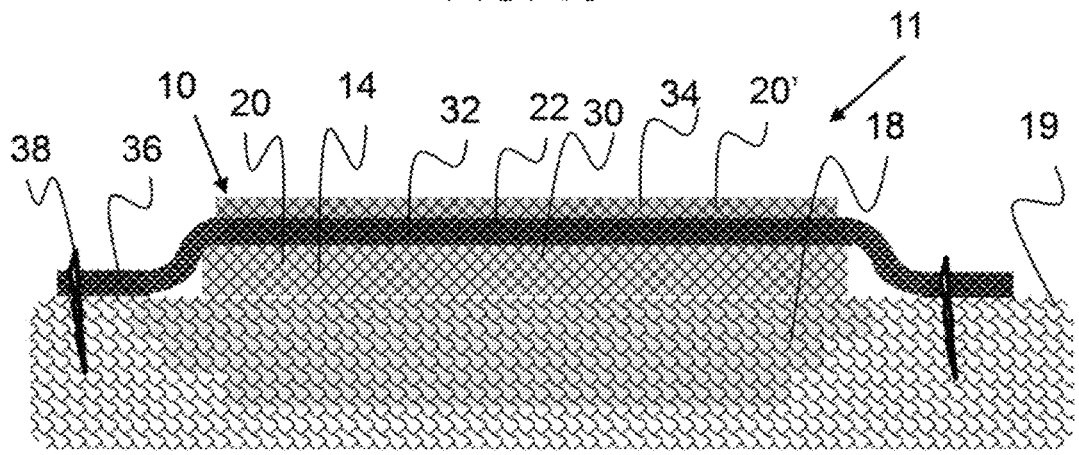

FIG. 14 shows a cross-sectional representation of an exemplary therapeutic composite configured over a treatment location wherein the therapeutic composite comprises a first matrix layer of amniotic membrane imbibed with fluid component, a second matrix layer that is a support layer and a third matrix layer that comprises amniotic membrane.

Figure 15:
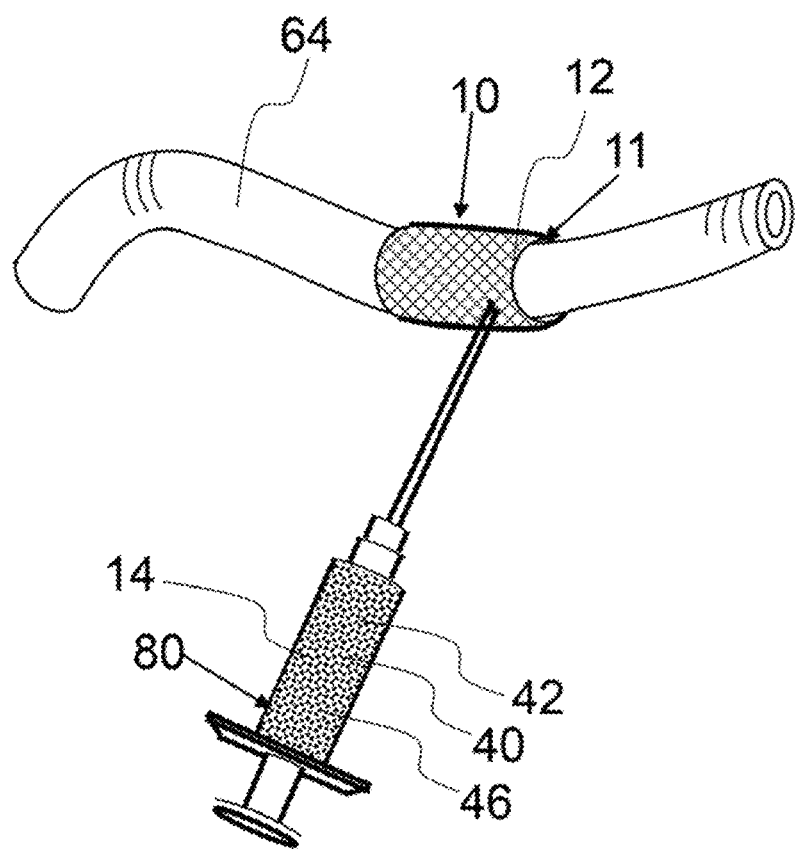

FIG. 15 shows an exemplary matrix component of a therapeutic composite configured around an artery and a fluid component being injected therein.

Figure 16:
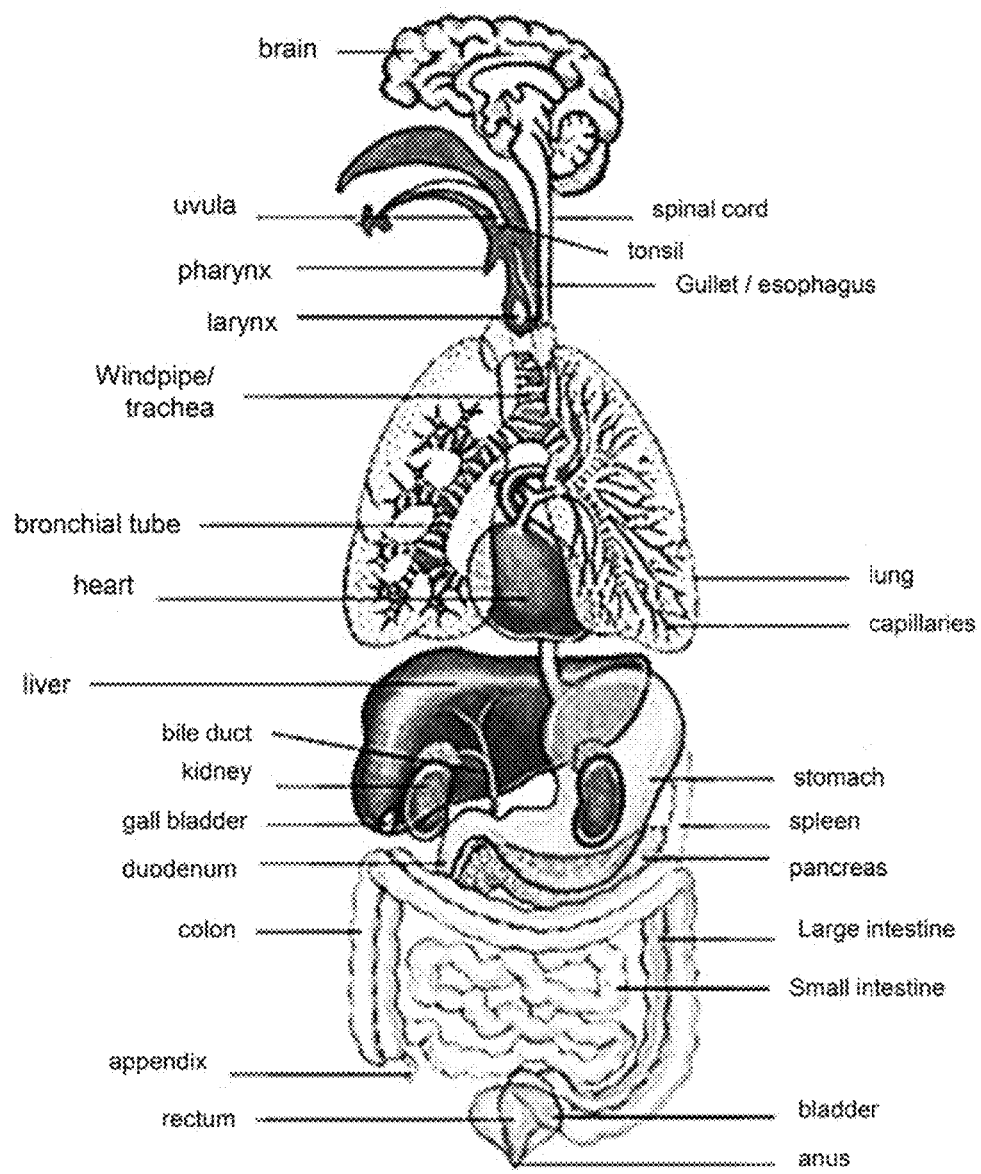

FIG. 16 shows a diagram of the anatomy and various organs within the body.

Figure 17:
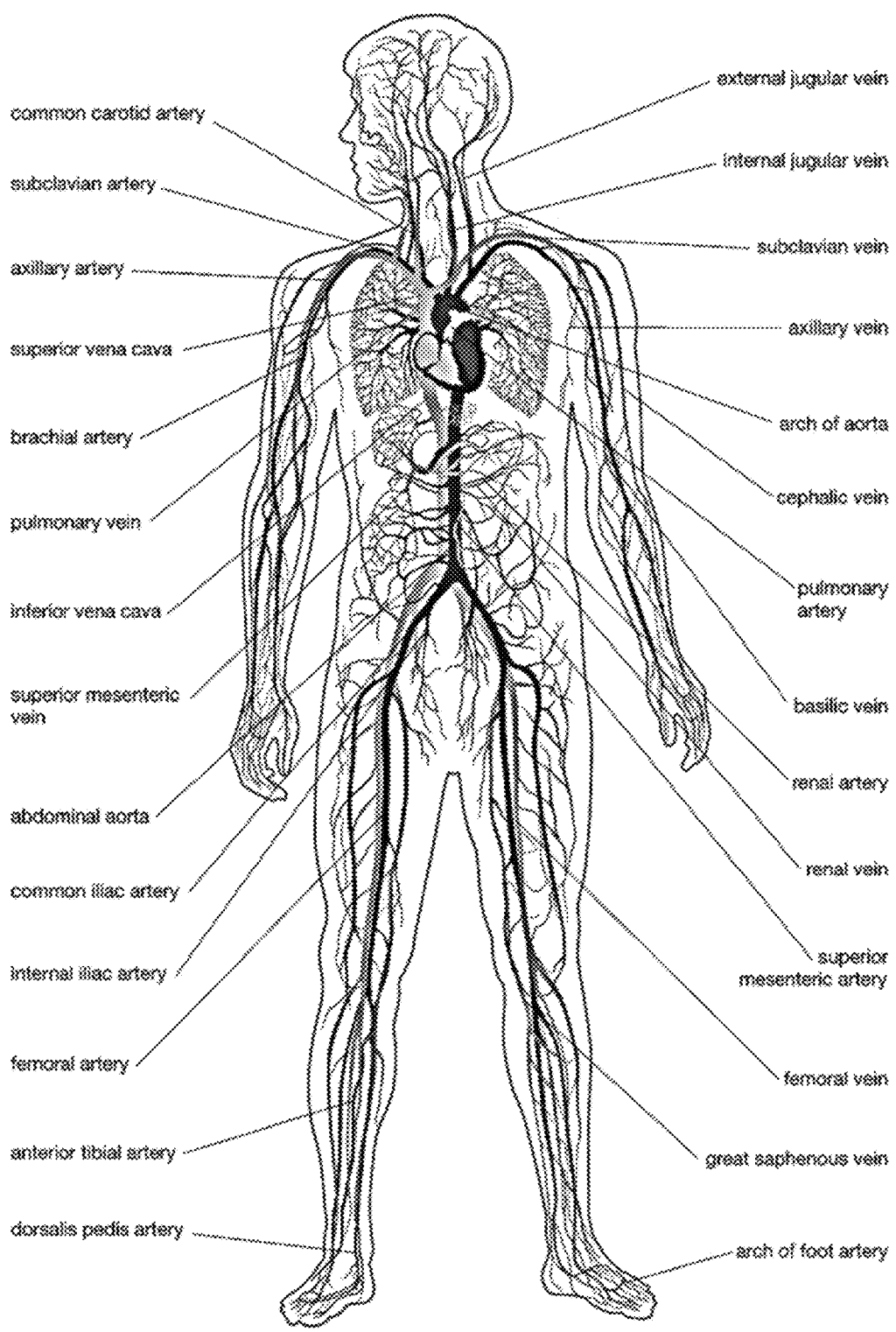

FIG. 17 shows a diagram of the circulatory system.

Figure 18:
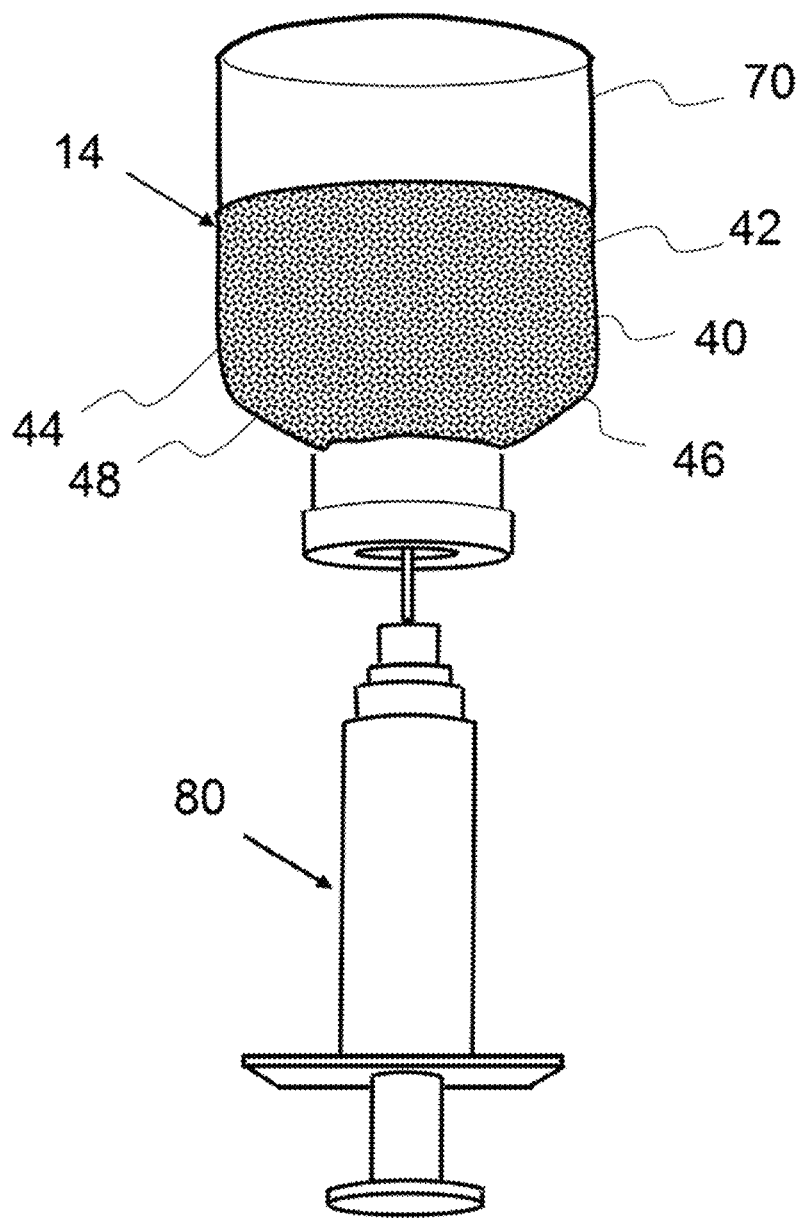

FIG. 18 shows an exemplary fluid component being drawn from an enclosure by a syringe.

Figure 19:
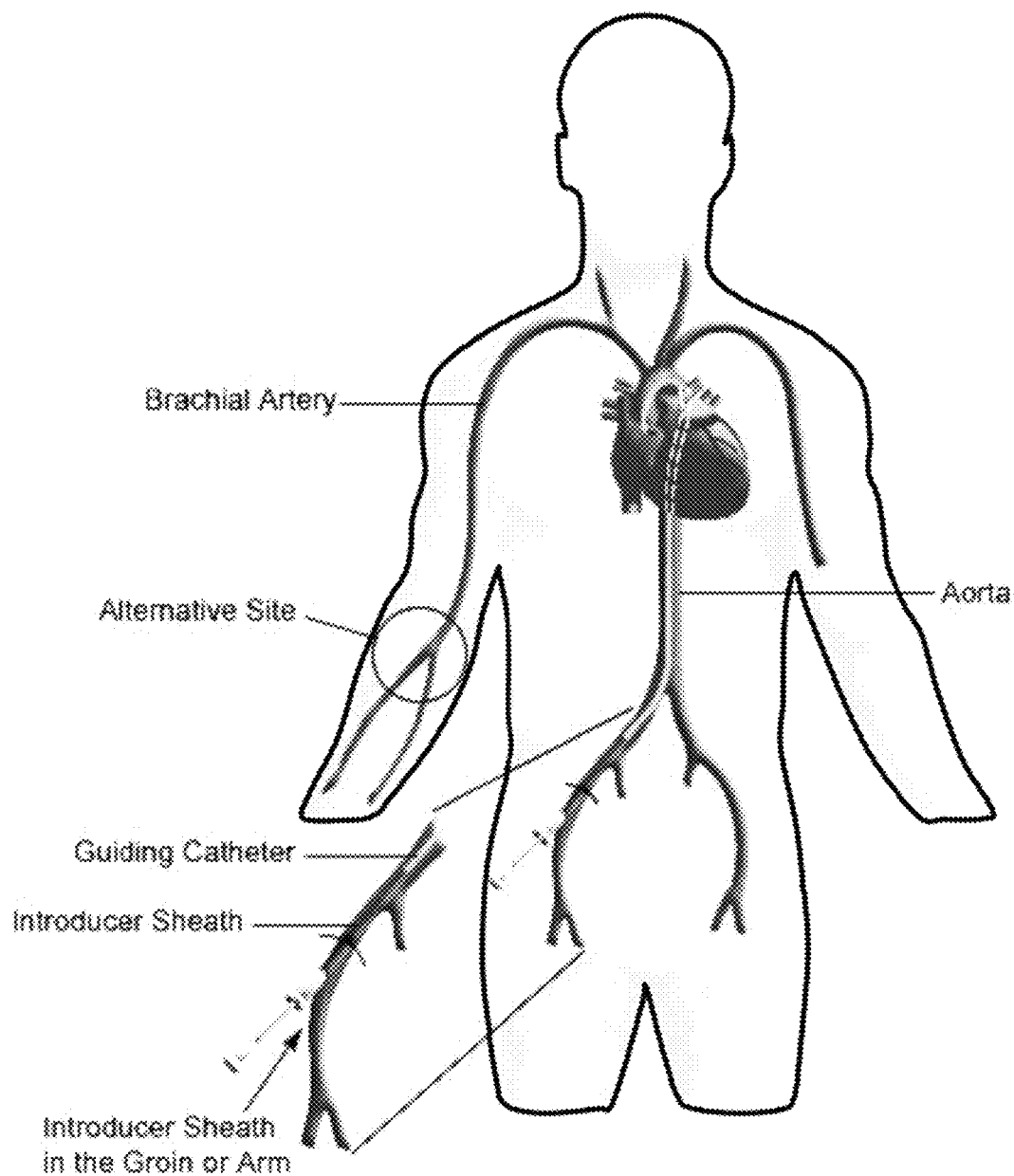

FIG. 19 shows an exemplary catheter inserted through the femoral artery with the proximal end located at the heart.

Figure 20:
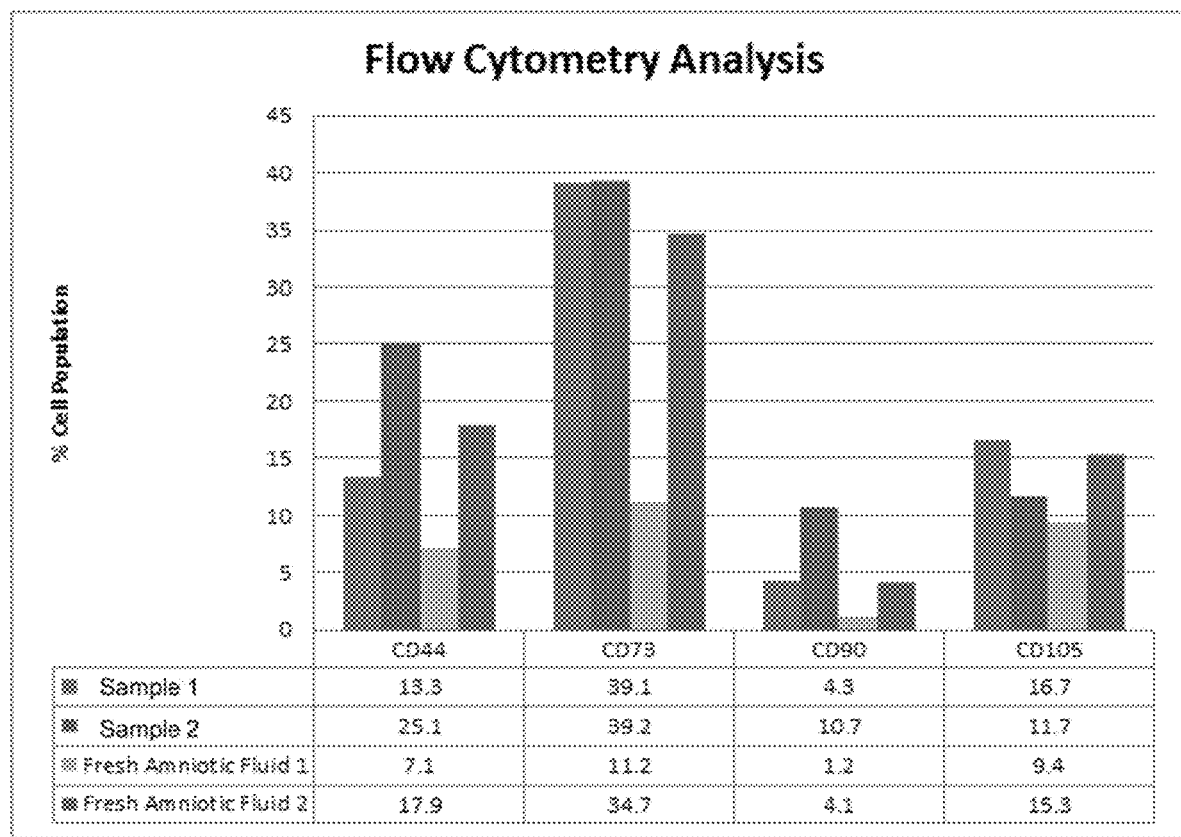

FIG. 20 shows flow cytometry analysis data for amniotic fluid as received and amniotic stem cell concentrated fluid.

Figure 21:
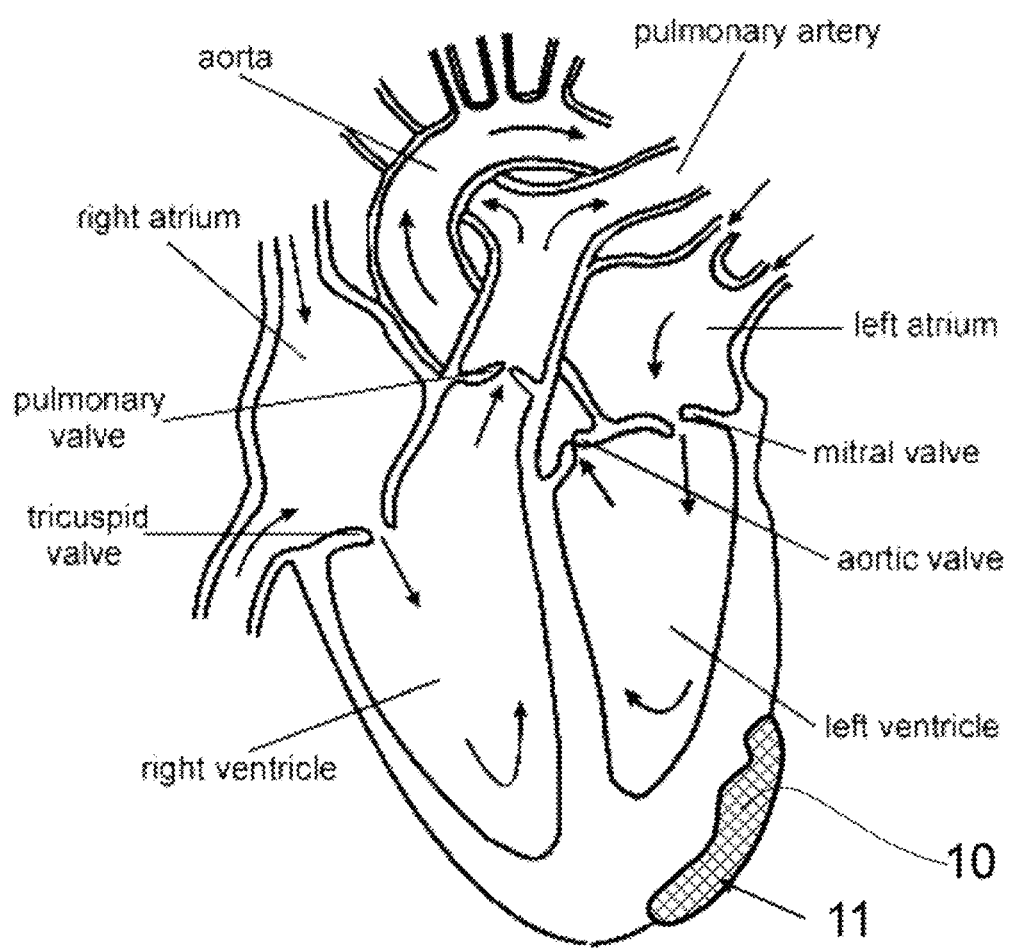

FIG. 21 shows a cross-sectional view of a heart.

Figure 22:
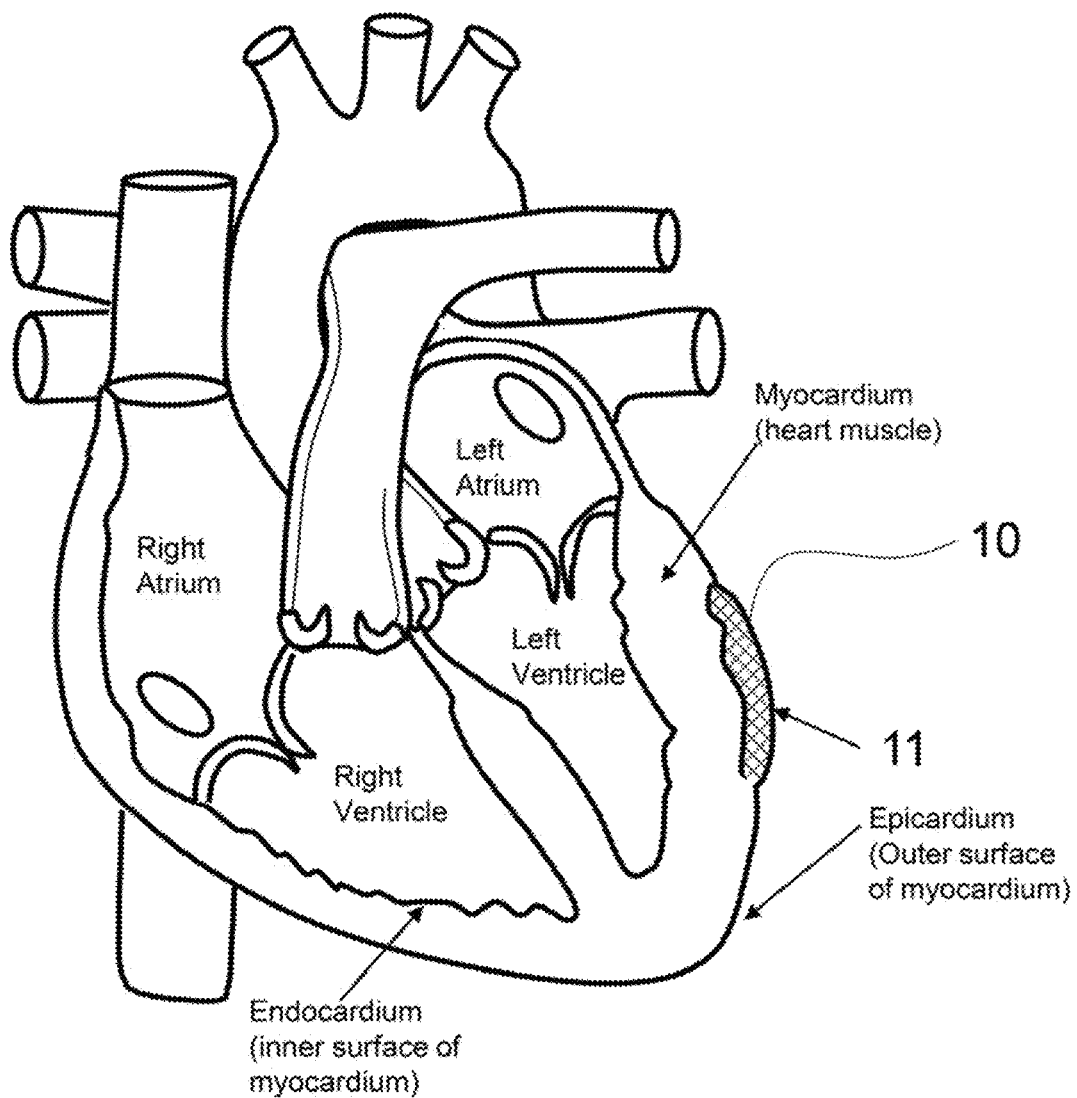

FIG. 22 shows a cross-sectional view of a heart with an exemplary therapeutic composite placed on the epicardium.

Figure 23:
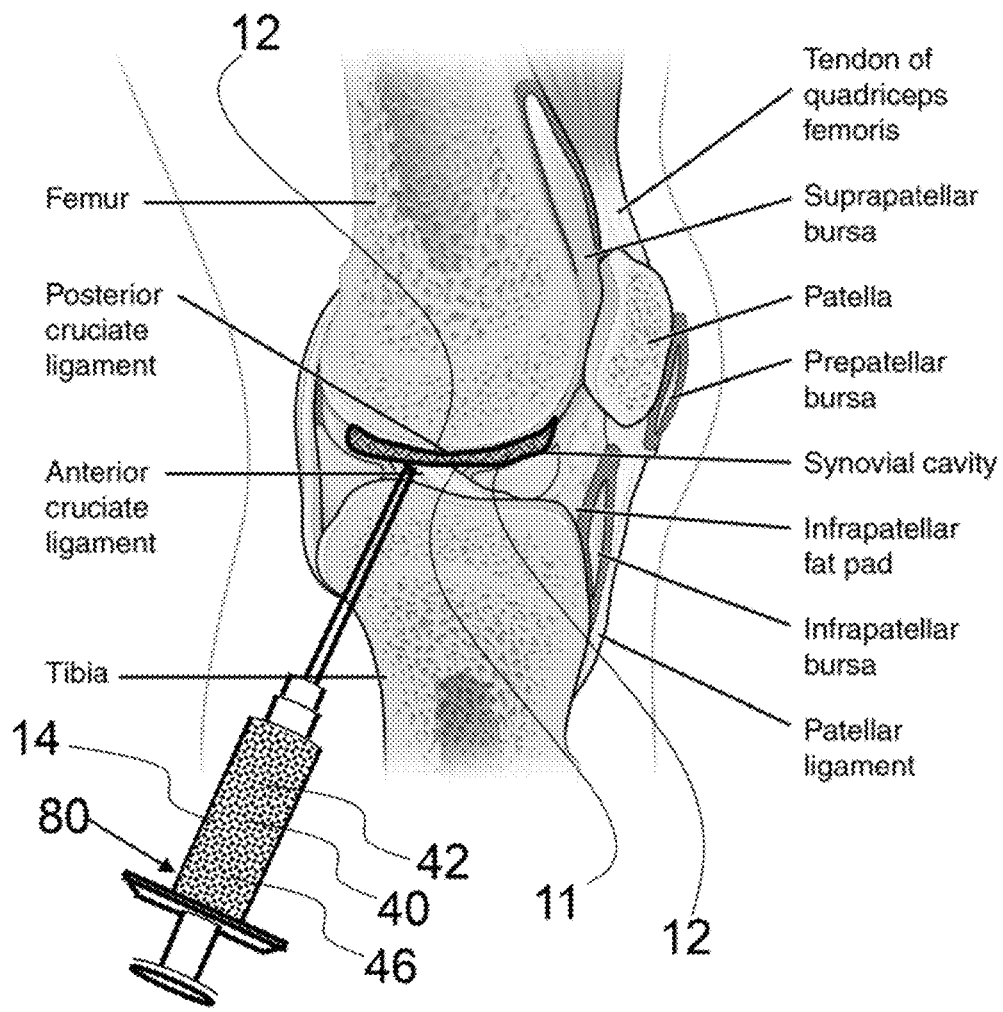

FIG. 23 shows a knee joint having an exemplary therapeutic composite configured therein and a syringe injecting fluid component into the matrix component.

Figure 24:
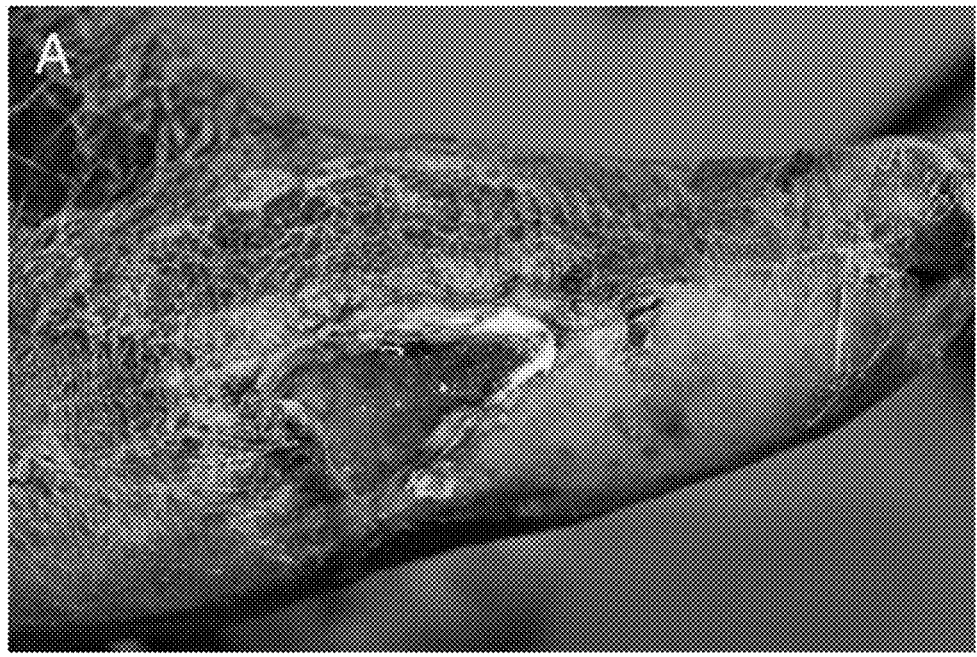

FIG. 24 shows a picture of a wound on a diabetic person's foot prior to treatment.

Figure 25:
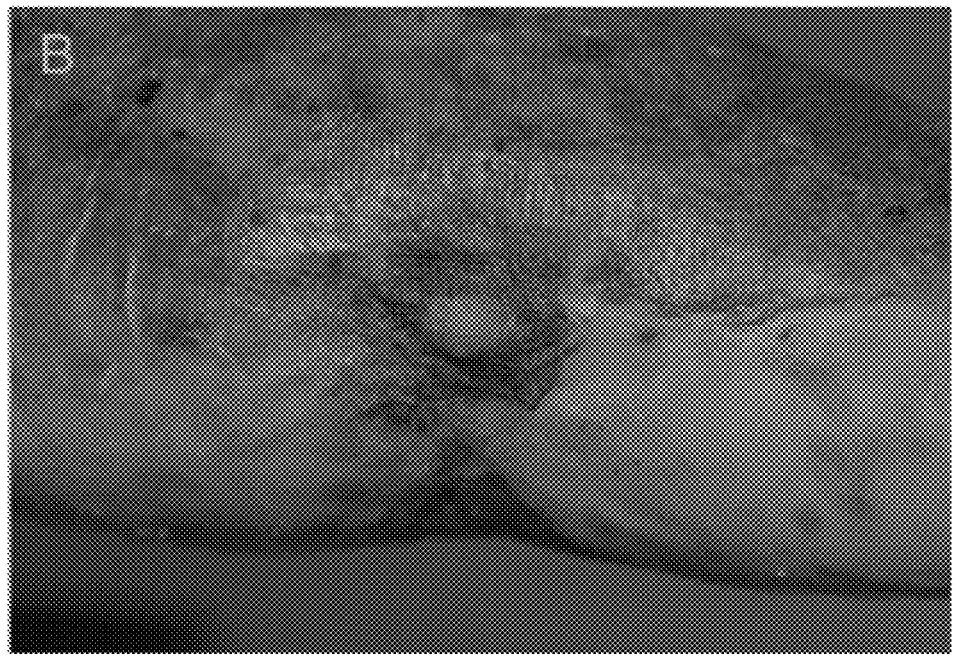

FIG. 25 shows a picture of the wound shown in FIG. 19A after 57 days of treatment with an exemplary therapeutic composite as described herein.

Figures 26, 27:

FIG. 26 shows an x-ray of an osteochondral defect in an ankle, prior to treatment.

FIG. 27 shows an x-ray of an osteochondral defect in an ankle, prior to treatment.

Figure 28:
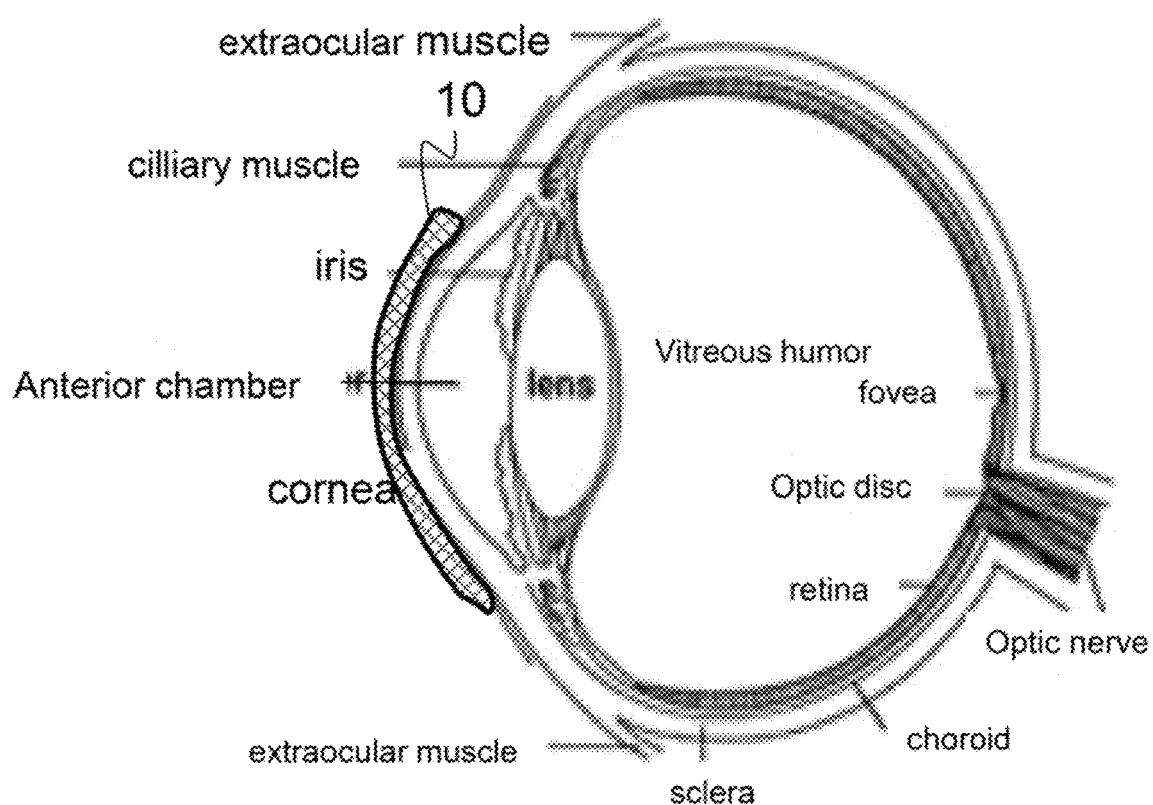

FIG. 28 shows a cross-sectional view of an eye.

Figure 29:
Figure 30:
Figure 31:
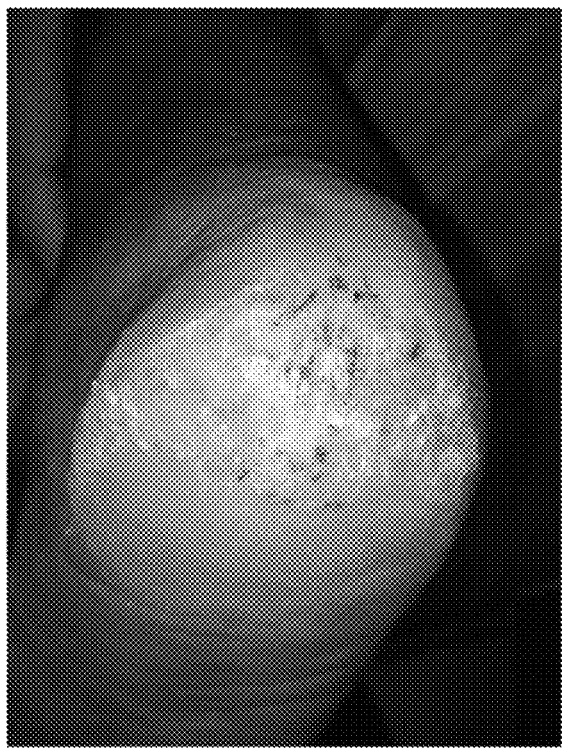

FIGS. 29-31 show black and white photographs of a wound on a heel and the progression of healing with application of a therapeutic composition, as described herein.

Figure 32:
Figure 33:

FIG. 32 shows a black and white photograph of a patient with late-stage fibrosis and FIG. 33 shows the therapeutic effect of application of a therapeutic composition to the scar.

Figure 34:
Figure 35:
Figures 36, 37:

FIGS. 34 and 35 show X-rays of a patient with arthroscopy chondroplasty and FIGS. 36 and 37 shows X-rays of said patient six months post operation in which a therapeutic composition was applied.

Corresponding reference characters indicate corresponding parts throughout the several views of the figures. The figures represent an illustration of some of the embodiments of the present invention and are not to be construed as limiting the scope of the invention in any manner. Further, the figures are not necessarily to scale, some features may be exaggerated to show details of particular components. Therefore, specific structural and functional details disclosed herein are not to be interpreted as limiting, but merely as a representative basis for teaching one skilled in the art to variously employ the present invention.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

Certain exemplary embodiments of the present invention are described herein and illustrated in the accompanying figures. The embodiments described are only for purposes of illustrating the present invention and should not be interpreted as limiting the scope of the invention. Other embodiments of the invention, and certain modifications, combinations and improvements of the described embodiments, will occur to those skilled in the art and all such alternate embodiments, combinations, modifications, improvements are within the scope of the present invention.

As shown if FIG. 1A the amniotic membrane surrounds a fetus in utero. As shown in FIG. 1B, the amniotic membrane comprises an amnion portion and a chorion portion. As described herein, the amnion portion may be separated from the chorion. In an exemplary embodiment, the epithelium, or inner most layer of the amniotic membrane, is removed and used to produce particles for the therapeutic composite, as described herein. The particles may consist essentially of the epithelium, consists essentially of the epithelium and base membrane, consist essentially of the epithelium, base membrane and compact layer, or consist essentially of epithelium, base membrane, compact layer, and fibroblast layer.

As shown in FIGS. 2A and 2B, the epithelium layer of the amniotic membrane 20 has a single layer of amniotic stem cells 46. The tissue around the amniotic stem cells may protect and enhance the viability of these stem cells when the epithelium is cryo-fractured to produce particles for the therapeutic composition.

As shown in FIG. 3A, an amniotic membrane 20 comprises a plurality of amniotic stem cells 46.

As shown in FIG. 33, particles of cryo-fractured amniotic membrane particles 40 are on the order of 0.2 to 0.5 μm in size. The average particle size shown is less than 2 μm. There are no particles shown that are larger than 2 μm and substantially all of the particles are less than 1 μm in size. The SEM shows that the micronized amniotic membrane particles are irregularly shaped. As shown, some of the particles have a planar surface.

As shown in FIG. 4 an amniotic membrane 20 comprises pores 29 between the amniotic membrane tissue. This porosity may be imbibed with a fluid component. In addition, an amniotic membrane may be stretched in one or more direction to tensilize the tissue. A tensilized amniotic membrane may have a higher matrix tensile strength than an original un-tensilized amniotic membrane. In addition, a plurality, of layers of amniotic membrane may be utilized to build strength in one or more directions.

As shown in FIG. 5A, an amniotic membrane 20 has been stretched in one direction to form an elongated and more aligned amniotic tissue orientation. As shown in FIG. 5A, oriented tissue 23 is aligned horizontally and connecting tissue interconnects the oriented tissue. A tensilized amniotic membrane 21 may be stronger by unit weight in the oriented direction and may have a much higher elongation to break in the cross-oriented direction than a precursor amniotic membrane, before tensilizing. The tensilized amniotic membrane 21 may be stretched as much as 120%, 150%, 175%, 200% of the original membrane length. The amniotic membrane may neck or narrow in the opposing direction of stretch. A stretched or tensilized amniotic membrane may be stretched over a long period of time to minimize tissue fracture. For example, an amniotic membrane may have a low load applied and may be stretched over a period of 10 minutes or more, 30 minutes or more, 1 hour or more, 6 hours or more, 1 day or more, 2 days more and any range between and including the durations provided. In addition, an amniotic membrane may be stretched while being hydrated and or submerged in amniotic fluid or a plasticizing fluid. An amniotic membrane may be cross-linked after being stretched. The load applied to tensilize an amniotic membrane may be a portion of the maximum tensile load required to fracture the amniotic membrane at a rate of 10 mm/second for a 2.54 cm by 15.2 cm sample having a 5 cm gap. For example, a tensilizing load applied may be no more than about 80%, no more than about 60% no more than about 50%, no more than about 25% of the maximum tensile load.

As shown in FIG. 5B, a first tensilized amniotic membrane 20 is configured at a 90 degree offset from a second amniotic membrane 20'. This orientation of layering may provide for a much stronger therapeutic composite. In an alternative embodiment, a plurality of layers of tensilized amniotic membrane may be aligned with the oriented tissue of a first layer being aligned with the oriented tissue of a second layer. A matrix component or a therapeutic composite as described herein, may consist essentially of tensilized amniotic membrane.

FIG. 6 shows a diagram of an exemplary method to apply a therapeutic composite as described herein. As described herein, a fluid component may be configured with a matrix component or may be applied after application of the matrix component to a treatment location.

As shown in FIG. 7, a process to produce a therapeutic composition, as described herein, comprises the steps of cryo-fracturing amniotic membrane fragments. As described, the amniotic membrane fragments may be cryo-fractured with a blunt object, such as a bar, that reduces shear and damage to the particles. In a preferred embodiment, the fragments are cryo-fractured with an object having substantially no sharp edges. The micronized particles are combined with any suitable carrier fluid to produce a therapeutic composite. In an exemplary embodiment, the micronized particles are dispersed in a fluid comprising stem cell fluid and amniotic stem cells. In another embodiment, the micronized particles are dispersed in a concentrated amniotic stem cell fluid.

As shown in FIG. 8, a process to produce a therapeutic composition, as described herein, comprises the steps concentrating amniotic stem cells in an amniotic fluid. An amniotic fluid may be processed in any suitable way to concentrate the amniotic stem cells in the fluid. In an exemplary embodiment, as described in FIG. 5, the amniotic fluid is centrifuged to remove debris and excess liquid and concentrate the amniotic stem cells in the therapeutic composition.

As shown in FIG. 9, an exemplary therapeutic composition 11 is a therapeutic composite 10. The therapeutic composite 10 comprises an amniotic membrane 20, as a matrix component 12, configured over a treatment location 18. The matrix component 12 in this embodiment consists essentially of amniotic membrane 20 and a fluid component 14 is coated onto the treatment surface 50 of the therapeutic composite. The fluid component 14 is not present on the outer surface 52 of the therapeutic composite 10.

As shown in FIG. 10, an exemplary therapeutic composite 10 comprises an amniotic membrane 20 and a fluid component 14 imbibed therein, configured over a treatment location 18. The fluid component 14 comprises micronized amniotic membrane particles 40 and amniotic fluid 43. However, any suitable fluid carrier may be used to disperse the micronized amniotic membrane particles and or amniotic stem cells 46.

As shown in FIG. 11, an exemplary therapeutic composite 10 is configured over a treatment location 18 wherein the therapeutic composite comprises an amniotic membrane 20 imbibed with a fluid component 14 and a cover layer 24 is configured there over. The matrix component 12 comprises a first matrix layer 30 and a second matrix layer 32. The second matrix layer is configured over said first matrix layer and comprises an overhang portion 36 that extends outside of the first matrix layer. The second matrix layer is attached to the tissue 19 by a attachment component 38, such as a staple, glue and/or sutures, for example. A matrix component or a layer of a matrix component may be configured to extend beyond a treatment location, whereby an outer area of the matrix component can be affixed to tissue. A cover layer may fully cover a first or under layer of matrix component or may only cover a portion of a layer thereunder. A cover layer may be a net or mesh or strands that extend across and over an under-layer, for example. An exemplary cover layer comprises pores or apertures 28 that allow fluid transfer to and from the treatment location. Apertures may be small slits, holes, in an otherwise solid and impermeable matrix component or layer, or they may be pores in porous matrix component or layer. For example, an expanded polytetrafluoroethylene membrane may have a mean flow pore size as measure by a Coulter Porometer (PMI Industries), of less than 50 um, less than 40 um, less than 10 um, less than 1 um and any range between and including the pore sizes provided. In one embodiment, the pores are sized to allow fluid to flow but retain cells, such as stem cells within the matrix component.

As shown in FIG. 12, an exemplary therapeutic composite 10 is configured over a treatment location 18 wherein the therapeutic composite comprises a matrix component 12 comprising a first matrix layer 12 of amniotic membrane 20, a second matrix layer 32 of a fluid reservoir layer 25, and a third matrix layer 34 that is a cover layer 24. The fluid reservoir layer comprises a matrix having porosity containing a fluid component 14', as described herein. As shown, a first fluid component 14 is configured within the first matrix layer 30. It is be noted that different compositions of a first and second fluid component may be configured in a matrix component 12. A first fluid component may comprise an amniotic stem cell concentrated fluid and a second fluid component may comprise micronized amniotic membrane dispersed in a fluid, for example. A reservoir layer may comprise a fluid component having stem cells, and these stem cells may be drawn from the reservoir layer as they are needed.

As shown in FIG. 13, a therapeutic composite 10 is configured over a treatment location 18 wherein the matrix component 12 comprises a first matrix layer 30 of amniotic membrane 20 imbibed with fluid component 14 and a second matrix layer 32 that is a support layer 22 comprising bioresorbable material 26. The support layer may be substantially impermeable to the fluid component configured in the first matrix component that is proximate a treatment location. In addition, an outer surface 52 of a matrix component 12, or the surface facing away a treatment location, may be hydrophobic to reduce fluid ingress into the therapeutic composite. Bodily fluid ingress into a therapeutic composite may dilute a fluid component comprises therein.

As shown in FIG. 14, an exemplary therapeutic composite 10 is configured over a treatment location 18 wherein the matrix component 12 comprises a first matrix layer 30 of amniotic membrane 20 imbibed with fluid component 14, a second matrix layer 32 that is a support layer 22 and a third matrix layer 34 that comprises amniotic membrane 20. A support layer is configured between amniotic membranes in this embodiment. As described herein, a matrix component may be provided with multiple layers attached and ready for orientation on a treatment location, or a plurality of matrix components may be applied, one after another, during the treatment procedure.

Any number of combinations of matrix components layers have been envisioned and are within the scope of the present invention. In addition, any number of different fluid components may be incorporated into a therapeutic composite as described herein.

As shown in FIG. 15, an exemplary therapeutic composite 10 is configured around an artery 64 and a fluid component 14 is being injected therein. This type of procedure may reduce and/or eliminate aneurisms. A matrix component may be a sheet of material having a substantially planar top and bottom surface and substantially uniform thickness therebetween. A sheet of matrix composite may be supple and may be configured around a cylindrical treatment location, such as an artery or vein. In another embodiment, a matrix component sheet is applied externally over a treatment location, such as to the epicardium.

FIG. 16 shows a diagram of the anatomy and various organs within the body that may be treated with a therapeutic composite as described herein. A therapeutic composite, as described herein, may be introduced into any anatomy shown in FIG. 16 by open surgery, topical application, or transcatheter. A deliver vehicle such as a stent or balloon may be used with a therapeutic composite, as described herein. For example, a therapeutic composite may be introduced into any portion of the urinary or digestive system, including the bladder, ureter, urethra, small intestine, large intestine, stomach, esophagus, mouth, tongue, colon, rectum, and the like.

FIG. 17 shows a diagram of the circulatory system where a therapeutic composite may be introduced into the body through transcatheter.

FIG. 18 shows an exemplary fluid component 14 being drawn from an enclosure 70 by a syringe 80. The fluid component comprises micronized particles 40 of amniotic membrane 20 and stromal vascular fraction 48 in a concentrated amniotic stem cell fluid 44. The needle may be any suitable size, however in a preferred embodiment the needle is no larger than a 20 gauge needle.

As shown in FIG. 19, a catheter is inserted into the femoral artery and the proximal end of the catheter is located at the heart. A therapeutic composite may be introduced through a catheter to a treatment location within the body. A catheter may be configured with an injection implement at the proximal end to enable the therapeutic composite to be injected into tissue, such as heart tissue.

FIG. 20 shows flow cytometry analysis data for amniotic fluid as received and amniotic stem cell concentrated fluid as described herein. Flow cytometry was performed on four different liquid samples from different donors. The analysis shows that the expression level of mesenchymal stem cell surface antigens is consistent between donors with CD44 being positive and CD73 being strongly positive while CD90 and CD105 are low positive. The level of expression is maintained between the processed samples concentrated sample 1 and concentrated sample 2 and unprocessed samples (Fresh Amniotic Fluid 1&2), suggesting no cell loss during the manufacturing process and preservation of potency. What is also interesting is that CD73 is expressed the most. It has been reported that mesenchymal stem cell migration is controlled by CD73 and therefore it is speculated that a high level of CD73 expression promotes cell migration and the ability of the cells to home to tissue sites of repair or to participate in healing responses.

FIGS. 21 and 22 show cross-sections of a heart and some of the treatment locations for a therapeutic composite, as described herein. For example, therapeutic composite 10 may be placed on the epicardium, as shown in FIG. 22, myocardium, and/or the endocardium to treat arrhythmia or post-operative atrial fibrillation, for example. The therapeutic composite may have a fluid component, or a fluid component may be applied subsequent to placement of the matrix component on the heart.

As shown in FIG. 23, a knee joint has an exemplary therapeutic composition 11 configured therein comprising a matrix component and a fluid component 14, therein forming a therapeutic composite 10. A syringe 80 is injecting a fluid component 14 into the matrix component 12. As described herein, a fluid component may be applied into or around a matrix component during or after an initial therapeutic procedure to position a matrix component on a treatment location. The fluid component 14 shown in FIG. 23 comprises micronized amniotic membrane particles 40, and amniotic stem cells 46 dispersed in a fluid 42. A syringe may be used to inject a fluid component periodically after an initial procedure.

As shown in FIG. 24, a wound on a diabetic person's foot prior has a length of approximately 11 mm and width of approximately 7 mm. As shown in FIG. 19B, the wound has healed considerably after 57 days of treatment with an exemplary therapeutic composite as described herein. A therapeutic composite of amniotic membrane was placed over the wound along and a fluid component comprising micronized amniotic membrane and a concentrated amniotic stem cell fluid was applied topically. The fluid component described was applied topically over a 57 day period, over which the wound healed as shown in FIG. 25.

As shown in FIG. 26 a patient has an osteochondral defect in an ankle, with some bone degradation. A therapeutic composite was applied over the defect and a fluid component was then applied to the treatment site.

FIG. 27 shows the improvement in the defect including tissue regeneration and reduction of the defect area and volume.

FIG. 28 shows a cross-sectional diagram of an eye and some of the treatment locations for a therapeutic composite, as described herein. For example, a therapeutic composite 10, as described herein, may be applied topically over the cornea and a fluid component may be added periodically to promote healing and reduce scaring.

As shown in FIG. 29, a patient had a deep cut in their heel. A therapeutic composition comprising a fluid component comprising amniotic fluid and micronized amniotic membrane particles, as generally described in Example 1, was injected around the cut. The wound was fully evaluated to insure no osteomyelitis. The wound was cleaned to remove any debris and then covered with a dressing. The therapeutic composition was injected in approximately equal amounts around the periphery of the cut. Approximately 1 ml of therapeutic composition having approximately 8 sq cm of micronized membrane was mixed with an equal volume of saline. Four injections were made, about equally spaced, around the perimeter of the wound. The injections were made approximately 6 to 8 mm from the edge of the wounds and in a direction toward the wound. About 0.5 ml of the therapeutic composition and saline mixture was dispensed in each injection location. The wound was then covered with a non-stick dressing. After approximately 38 hours, the dressing was removed from the wound and the wound was washed and covered with a new dressing. The wound shown in FIG. 31 was substantially closed after only 13 days from the injection. However, in the event that the wound is not closed another injection may be administered as needed. n an alternative embodiment, an amniotic membrane may be applied over a cut or wound and a fluid component, such as that described in Example 1, may be injected around the wound as described herein.

FIG. 32 shows a black and white photograph of a patient with late-stage fibrosis and FIG. 33 shows the therapeutic effect of application of a therapeutic composition to the scar. FIG. 32 shows an image of a person's chest having an involuted scar at the location of a previous tube insertion. The patient had a lot of pain from this scar and internal adhesions. A therapeutic fluid was injected into the scar area and the scar adhesions were released, the tissue was remodeled, and pain was reduced. FIG. 33 shows the dramatic improvement of the scar.

FIGS. 34 and 35 show X-rays of a patient with stage 4 osteoarthritis. FIGS. 36 and 37 shows X-rays of said patient 6 months post arthroscopy chondroplasty procedure in which a therapeutic composition was introduced to the joint. FIG. 34 shows pre-operative image of the tibia, talus and the calcaneus bone on bone affected area. After application of a therapeutic composition, as described in detail in Example 3, the joint between was widened and restored as shown in FIGS. 36 and 37.

Example 1

Three fluid components were made and cell viability was measured as reported in Table 1. Three amniotic membrane samples, obtained from three separate donors, were cryo-fractured and dispersed in fluid to create a fluid component, as described herein.

A fluid component of the therapeutic composite was prepared by concentrations of amniotic stem cells in a cell suspension solution. A 1 ml. sample of an unprocessed, amniotic fluid was used to measure initial cell count and viability The amniotic fluid was then separated into 50 ml sterile centrifuge tubes and centrifuged two times at 400×g for 10 minutes at ambient temperature. Cell pellet from each tube was washed with 20 ml of a cell suspension solution between centrifugation. Supernatant was removed and cells were re-suspended in a predetermined volume of cell suspension solution to obtain a final product cell concentration of $1 \times 10^6$ cell/mi.

Cryo-fractured particles of amniotic membrane were prepared for dispersion in the fluid component. Three amniotic membranes were obtained and rinsed using a cell suspension solution and transferred to a cutting board. Using blunt dissection, chorion was removed from the amniotic membrane and any remaining debris/blood was removed using sterile laps. The amniotic membrane dimensions were measured using a sterile stainless steel ruler. The amount of amniotic membrane needed to obtain an concentration of 1 cm$^2$/ml of therapeutic solution was retained and placed on a sterile drying rack and allowed to dry, for one hour. The amniotic membrane was then cut into small pieces, less than a 1 cm$^2$ and placed inside a milling chamber containing a blunt impactor. The cryo-mill used was from SPEX Sample Prep Inc., 6970EFM Enclosed Freezer/Mill Model 6970D.

The milling chambers were placed inside the cryomill and the amniotic membrane was micronized. The frequency of the impactor was 8 cycles per second, the precooling time was five minutes, the grinding time was three minutes and the intermediate cooling time was two minutes. After the micronization of the amniotic membrane was complete, the chambers were removed from the cryomill and allowed to warm at room temperature for one hour. The cryo-fractured amniotic membrane was then dispersed in 100 ml of fluid component prepared as described in this example. The final therapeutic composite was prepared by combining 100 ml or the fluid component and micronized amniotic membrane with equal volume (100 ml), of cryprotectant solution, CryoStor 10, available from Sigma-Aldrich. Using a repeater pipet, cryovials were then filled at the desired volume. The therapeutic solution was maintained at 4° C. during the vial filling process to preserve cell viability.

The cryovials were then cryopreserved using a controlled rate freezer. The controlled freezing protocol: cool at a rate of 1.0° C./min until chamber reached −4° C., cool at rate of 25.0° C./min until chamber reached −40° C., warm at a rate of 10.0° C./min until chamber reached −12° C., cool at rate of 1.0° C./min until chamber reached −40° C., and cool at rate of 10.0° C./min until chamber reached −90° C. Cryovials were then placed into cryo-boxes and transferred to a −80.0° C. freezer Thawing of the cryovials was performed and cell viability was again measured. Cell viability pre and post cryopreservation is reported in Table 1. The cryovials were removed from the −80.0° C. freezer and allowed to thaw at room temperature until the fluid components in the vial had a slushy consistency, or approximately three minutes for a 1 ml sample. An equal amount of cold Plasma Lyte-A was added to the sample for a 1:2 dilution. Samples were mixed and a small aliquot was used to perform cell count and viability enumeration. Cell count and viability was assessed using Trypan Blue.

Example 2

A prepared therapeutic composition, as described herein, comprising an amniotic membrane matrix component and a fluid component comprising amniotic fluid and micronized amniotic membrane was used to treat a heart after a coronary bypass graft surgery (CABG). During the concluding portion of a CABG and after the grafts were completed, a prepared amniotic membrane about 4 cm×8 cm in dimension, was placed onto the myocardium and held in place by hydrostatic tension. The fluid component contained a multitude of therapeutic components including growth factors including insulin, growth factor 1, transforming growth factor b1, cytokine proteins, collagen substrates, extracellular matrix proteins such as laminin, fibronectin annexin, vitronectin, and the like. These therapeutic components reduced inflammation, scarring and fibrosis of the myocardium. This reduced inflammation and fibrosis acted to ensure improved electrical activity of the heart (myocardium). This effect was documented on postoperative MRI that demonstrated the decreased fluid buildup, elimination of atrial fibrillation. The reduction of inflammation allowed normal electrical nerve impulses to be transmitted and long term MRI imaging at eight weeks revealed minimal scarring around the surgical site.

Example 3

Prophetic Example

Osteoarthritis is treated with a therapeutic composition, as described herein. Arthroscopic synovectomy was performed on the joint to remove debris, excess synovium and repair ligamentous instability. Arthroscopic chondroplasty was performed around to remove any free floating or unstable osteo-cartilage fragments. The subchondral bone was perforated with a drill or kirschner wire (0.035 inched or less) multiple times around and in the area of cartilage injury, allowing bone bleeding. Small perforations in the subchondral plate was necessary as larger disruptions will cause irregular joint cartilage to develop. The arthroscope was removed, and the portal to the joint was enlarged, converting to a small arthrotomy. An amniotic membrane was wrapped around an insert instrument, and after the insert instrument was inserted into the joint, the amniotic membrane was unfurled into the joint. The amniotic membrane was positioned over the injured and perforated cartilage. The insert instrument was removed and the portal to the joint was closed with traditional surgical techniques. After the portal was dosed, a fluid component, comprising 1 ml of micronized amniotic membrane in concentrated amniotic fluid having viable amniotic stem cells and 1 ml of saline, was injected into the operated joint using an 18-22 gauge needle on a syringe. X-rays of the affected joint before this procedure are shown in FIGS. 34 and 35. X-rays were taken of six months after the operation and the joint was widened and the tissue was remodeled as shown in FIGS. 36 and 37.

Definitions

Micronized particles, such as micronized amniotic membrane particles, as used her, means that the particles have an average particle size of no more than 1000 µm, particle size may be measured analysis of scanning micrograph.

It will be apparent to those skilled in the art that various modifications, combinations and variations can be made in the present invention without departing from the spirit or scope of the invention. Specific embodiments, features and elements described herein may be modified, and/or combined in any suitable manner. Thus, it is intended that the present invention cover the modifications, combinations and variations of this invention provided they come within the scope of the appended claims and their equivalents.

What is claimed is:

1. A method of making an amniotic fluid derived therapeutic composition comprising a heterogeneous population of primary cells with cell viability after a freeze-thaw cycle, the method comprising:
    a) providing an amniotic fluid comprising a fluid component and amniotic cells;
    b) measuring an initial cell count in the amniotic fluid to determine an initial cell concentration of amniotic cells;
    c) centrifuging a quantity of the amniotic fluid to separate the fluid component from the amniotic cells to produce
        (i) a quantity of an acellular amniotic fluid; and
        (ii) removed amniotic cells, the removed amniotic cells comprise a heterogeneous population of primary cells;
    d) adding a controlled number of said removed amniotic cells to a volume of carrier fluid to produce a concentrated composition having a calculated concentration of removed amniotic cells per volume of carrier fluid; and
    e) providing an amniotic membrane comprising an amnion layer and chorion layer, and wherein the amnion layer comprises epithelium,
    f) separating the amnion layer from the chorion layer;
    g) micronizing the amnion layer to produce micronized amniotic layer particles comprising:
        freezing said amniotic layer without a cryoprotectant to produce frozen amniotic layer;
        micronizing said frozen amniotic layer to produce said micronized amniotic layer particles that are free of cryoprotectant;
    wherein the micronized amniotic layer particles consist essentially of epithelium having a concentration of at least 70% epithelium;
    h) adding a controlled amount of micronized amniotic layer particles to the concentrated composition having a calculated concentration of removed amniotic cells per volume of carrier fluid to produce said amniotic fluid derived therapeutic composition having a calculated concentration of micronized amniotic layer particles and a calculated concentration of amniotic cells, wherein the micronized amniotic layer particles are free of chorion;
    wherein the amniotic fluid derived therapeutic composition has a concentration of micronized amniotic layer particles of at least 0.1 mg/ml of therapeutic composition;
    wherein the amniotic fluid derived therapeutic composition has a calculated concentration of removed amniotic cells between $0.25 \times 10^6$ to $10.0 \times 10^6$ per milliliter of carrier fluid;
    wherein the amniotic layer particles comprise micronized amniotic layer particles that have an average particle size of no more than lulu;
    wherein the method results in cell viability for the amniotic fluid derived therapeutic composition that is at least 50% after a freeze-thaw cycle.

2. The method of claim 1, wherein the amniotic fluid derived therapeutic composition has a calculated concentration of removed amniotic cells between $0.25 \times 10^6$ to $3.0 \times 10^6$ per milliliter of carrier fluid.

* * * * *